(12) United States Patent
Banerjee et al.

(10) Patent No.: US 10,220,410 B2
(45) Date of Patent: Mar. 5, 2019

(54) SYSTEMS AND METHODS FOR IN-SITU FORMATION OF NANOPARTICLES AND NANOFINS

(71) Applicant: The Texas A&M University System, College Station, TX (US)

(72) Inventors: Debjyoti Banerjee, College Station, TX (US); Byeongnam Jo, Ibaraki (JP); Jiwon Yu, Gyeongsangbuk-do (KR); Seunghwan Jung, Seoul (KR); Donghyun Shin, Arlington, TX (US); Saeil Jeon, Greensboro, NC (US); Seokwon Kang, Gyeonggi-do (KR)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 219 days.

(21) Appl. No.: 15/104,970

(22) PCT Filed: Dec. 15, 2014

(86) PCT No.: PCT/US2014/070378
§ 371 (c)(1),
(2) Date: Jun. 15, 2016

(87) PCT Pub. No.: WO2015/095068
PCT Pub. Date: Jun. 25, 2015

(65) Prior Publication Data
US 2016/0318067 A1    Nov. 3, 2016

Related U.S. Application Data

(60) Provisional application No. 61/916,537, filed on Dec. 16, 2013.

(51) Int. Cl.
*B05D 1/18* (2006.01)
*B05D 5/02* (2006.01)
(Continued)

(52) U.S. Cl.
CPC .............. *B05D 5/02* (2013.01); *A61K 9/1273* (2013.01); *A61K 9/5115* (2013.01);
(Continued)

(58) Field of Classification Search
CPC ............ B05D 1/18; B05D 5/02; B05D 7/227; A61K 9/5192
(Continued)

(56) References Cited

U.S. PATENT DOCUMENTS 5,759,230 A * 6/1998 Chow ....................... B22F 9/24
427/229
8,313,797 B2    11/2012 Mack et al.
(Continued)

OTHER PUBLICATIONS

PCT/US2014/070378 International Search Report and Written Opinion dated Mar. 27, 2015 (10 p.).
(Continued)

*Primary Examiner* — Kirsten Jolley
(74) *Attorney, Agent, or Firm* — Conley Rose, P.C.

(57) ABSTRACT

Systems and methods for forming nanoparticles in-situ are disclosed herein. The nanoparticles may be formed in-situ through thermocycling a solution comprising at least one of a molten salt, a surfactant, and a catalyst. The nanoparticles may form in the solution itself and/or on surfaces of a vessel in which the solution is formed. Nanofins may be formed from the agglomeration of particles in the solution and on surfaces. Microchannels may be formed by these nanofins, and in some cases microchannels on a surface may have nanofins form on the surface. In some embodiments, a previously formed solution that has nanoparticles formed in-situ may be used to generate nanofins in a vessel, on a wafer in a vessel, in the solution itself, or combinations thereof.

24 Claims, 15 Drawing Sheets

(51) Int. Cl.
 *B05D 7/22* (2006.01)
 *A61K 9/127* (2006.01)
 *A61K 9/51* (2006.01)

(52) U.S. Cl.
 CPC .............. *A61K 9/5192* (2013.01); *B05D 1/18* (2013.01); *B05D 7/227* (2013.01)

(58) Field of Classification Search
 USPC ........................................................ 427/230
 See application file for complete search history.

(56) References Cited

U.S. PATENT DOCUMENTS

| | | |
|---|---|---|
| 8,354,311 B2 | 1/2013 | Forbes |
| 2005/0126766 A1 | 6/2005 | Lee et al. |
| 2005/0129928 A1 | 6/2005 | Lee et al. |
| 2006/0254762 A1 | 11/2006 | Tao et al. |
| 2007/0140951 A1* | 6/2007 | O'Brien .................. A61K 8/19 423/592.1 |
| 2011/0088593 A1 | 4/2011 | Hemmati |
| 2011/0186789 A1* | 8/2011 | Samulski ............... B82Y 30/00 252/514 |
| 2013/0105135 A1 | 5/2013 | Kulah et al. |

OTHER PUBLICATIONS

Shin, Donghyun, et al., "Enhanced Specific Heat of Silica Nanofluid," Journal of Heat Transfer, Feb. 2011, vol. 133, No. 2, pp. 024501-1-024501-4 (4 p.).

Yu, Jiwon, et al., "Heat Transfer Measurements for Flow of Nanofluids in Microchannels Using Temperature Nano-Sensors," Frontiers in Heat and Mass Transfer, 2012, vol. 3, No. 1, pp. 1-9 (9 p.).

\* cited by examiner

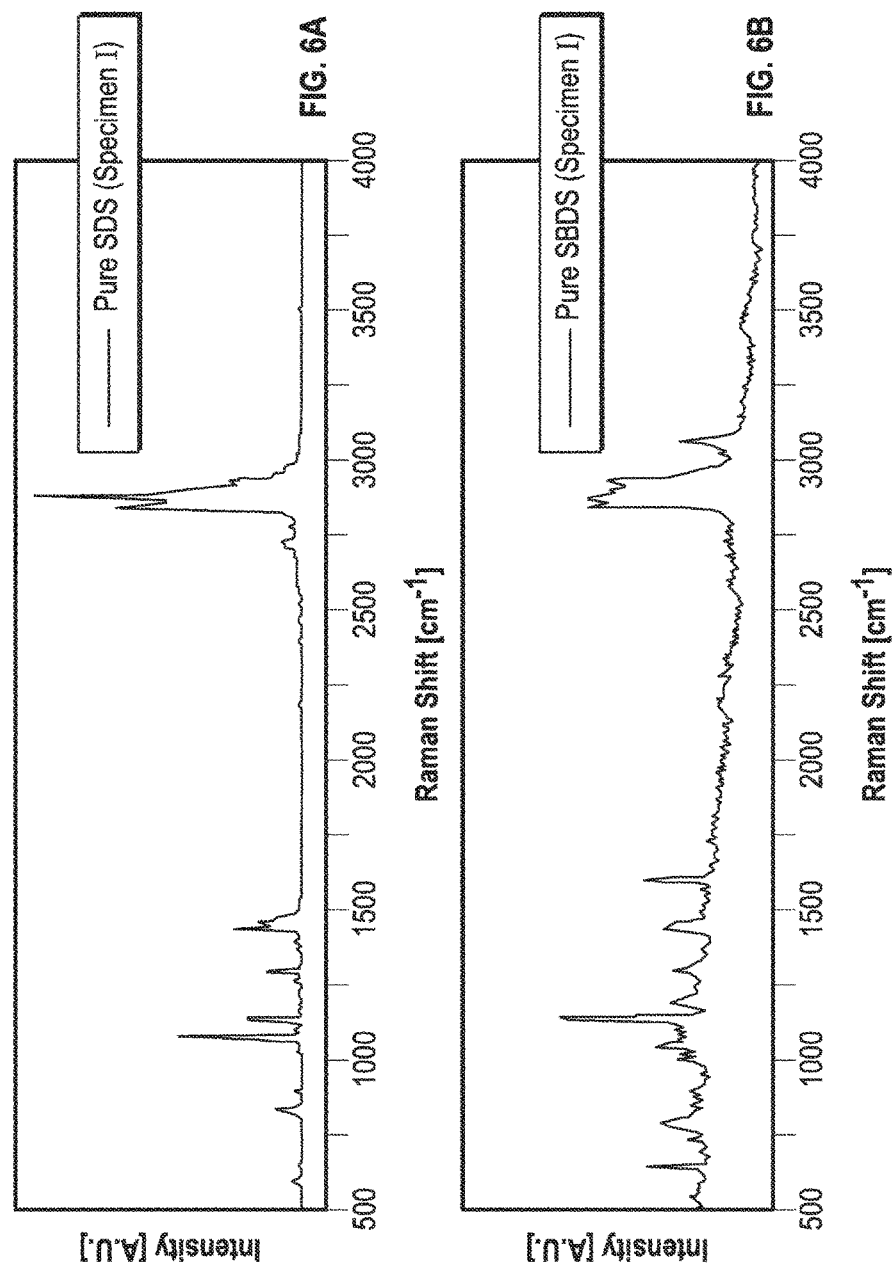

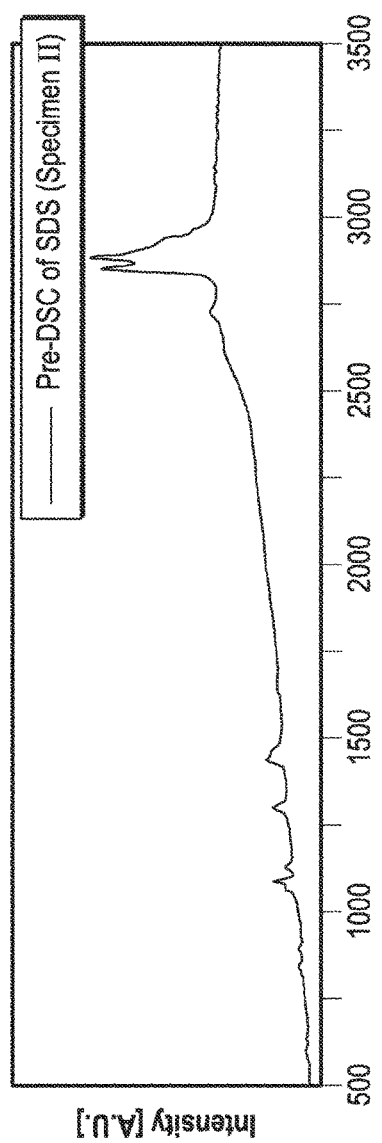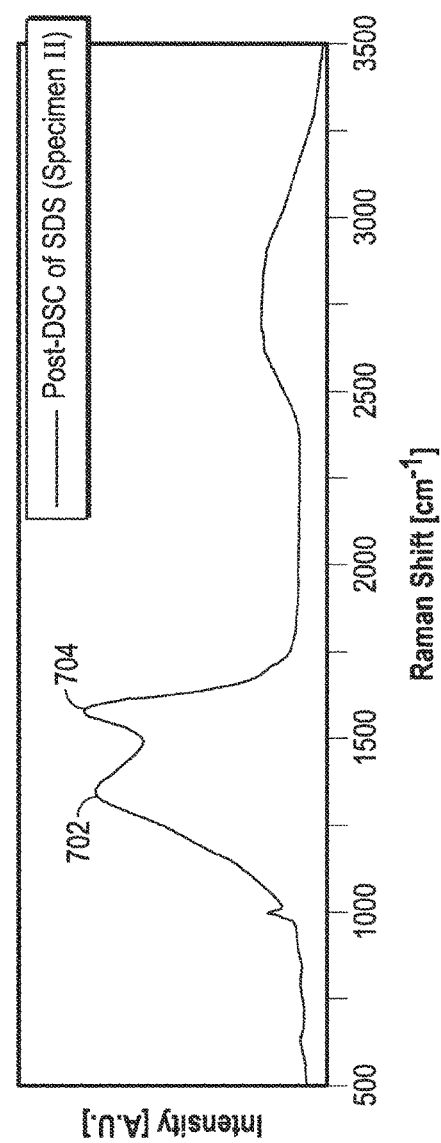

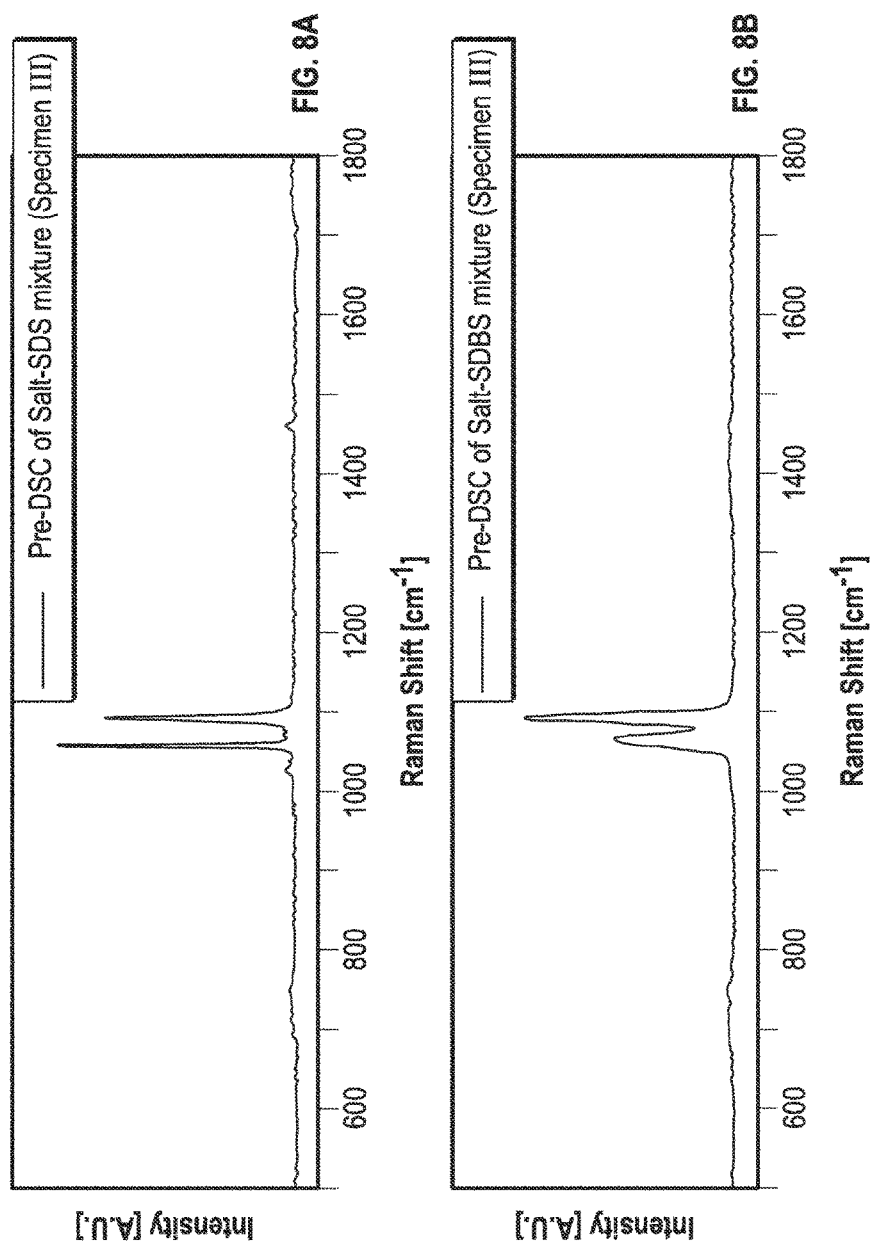

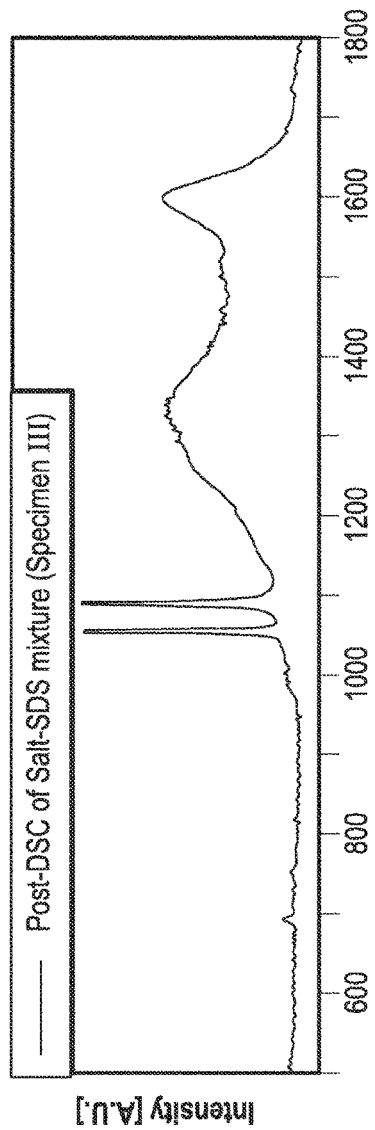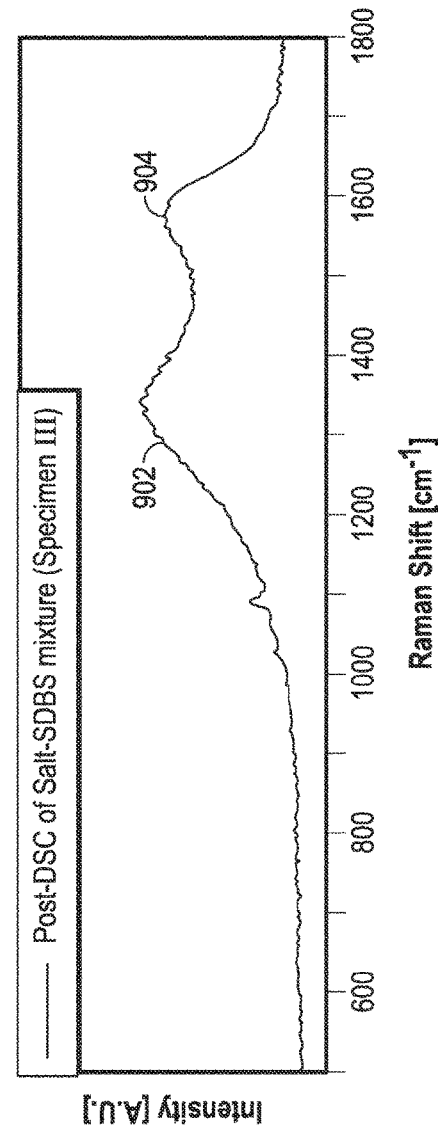

SYSTEMS AND METHODS FOR IN-SITU FORMATION OF NANOPARTICLES AND NANOFINS

CROSS-REFERENCE TO RELATED APPLICATIONS

This application is a 35 U.S.C. § 371 national stage application of PCT/US2014/070378 filed Dec. 15, 2014 and entitled, "Systems and Methods for In-Situ Formation of Nanoparticles and Nanofins," which claims benefit of U.S. provisional patent application Ser. No. 61/916,537 filed Dec. 16, 2013, and entitled "Systems and Methods for In-Situ Formation of Nanoparticles and Nanofins," each of which is hereby incorporated herein by reference in its entirety for all purposes.

STATEMENT REGARDING FEDERALLY SPONSORED RESEARCH OR DEVELOPMENT

This invention was made with government support under DE-FG36-08G018154 awarded by U.S. Department of Energy. The government has certain rights in the invention.

BACKGROUND

The disclosure relates generally to nanoparticles and nanofins. More particularly, this disclosure relates to energy storage and thermal management. Still more particularly, this disclosure relates to the removal of thermal energy in high heat flux devices as well as thermal energy storage for power generation and process industries such as heating, ventilation and air-conditioning systems ("HVAC" systems).

Many high heat flux devices such as integrated circuit chips for electrical/computation application, optical devices, and energy storage systems function optimally when there is a substantially uniform temperature distribution across the device. However, the operation of such devices often results in the generation of localized thermal energy. Consequently, mechanisms for transferring and distributing thermal energy within and from such devices are typically provided. In power generation systems, the power output often fluctuates based on the power demands. As a result, many power generation systems employ energy storage devices that store excess energy during periods when demand is relatively low to reduce fluctuations in power output. Often energy storage systems cost more than the power generation units themselves. Thus, techniques that can enhance the energy storage capacity of such systems offer the potential for lower cost of power generated and consumed due to better efficiency and coefficients of performance, respectively.

BRIEF SUMMARY OF THE DISCLOSURE

In an embodiment, a method for fabricating nanostructures comprising: (a) forming a homogeneous solution in a vessel, wherein the homogenous solution comprises a first component and a second component, and wherein the first component and the second component do not comprise nanoparticles; (b) evaporating at least some of a liquid in the homogenous solution after (a); (c) precipitating a first plurality of nanoparticles from the homogeneous solution in response to (a) or (b), wherein the first plurality of nanoparticles is formed on an interior surface of the vessel or in the homogeneous solution spaced apart from the interior surface of the vessel; and (d) forming a first plurality of nanofins on the interior surface of the vessel with the first plurality of nanoparticles after (c).

In an alternate embodiment, a method for fabricating nanostructures in-situ, the method comprising: (a) forming a solution in a vessel, wherein the solution comprises a surfactant; (b) after (a), precipitating a first plurality of nanoparticles from the solution onto an inner surface of the vessel after or within the solution; (c) evaporating at least some of a liquid in the solution after (b); (d) forming, in response to (b) or (c), a plurality of nanofins on a portion of the inner surface of the vessel with the first plurality of nanoparticles precipitated from the solution; and (e) forming a first plurality of channels on the portion of the inner surface of the vessel, wherein each channel of the first plurality of channels comprises at least some nanofins of the plurality of nanofins.

In an alternate embodiment, a method for fabricating nanostructures comprising: (a) disposing a substrate in a vessel and contacting an inner surface of the vessel with the substrate; (b) disposing a first component and a second component in the vessel to form a homogeneous solution in the vessel, wherein the first component and the second component do not comprise nanoparticles, and wherein the first component or the second component is a solution; (c) removing at least some of a liquid from the homogenous solution after (b); (d) precipitating a plurality of nanoparticles from the homogenous solution onto the inner surface of the vessel and the substrate in response to (b) or (c); (e) forming a plurality of nanofins on the inner surface of the vessel and on the substrate with the plurality of nanoparticles precipitated from the solution in (d); and (f) removing the substrate from the vessel after (e).

In an alternate embodiment, a method for fabricating nanofins from nanoparticles formed in-situ comprising: (a) forming a homogeneous solution comprising a first component and a second component in a vessel, wherein the first component comprises a plurality of nanoparticles formed in-situ in the first component; (b) precipitating a first plurality of nanoparticles from the homogeneous solution onto an inner surface of the vessel or in the homogeneous solution; (c) forming a first plurality of nanofins on an inner surface of the vessel with the first plurality of nanoparticles.

In an alternate embodiment, a method for fabricating nanostructures, comprising: (a) forming a homogeneous solution in a vessel, wherein the homogenous solution comprises a first component, a second component, and a third component, wherein the first component and the second component do not comprise nanoparticles, and wherein the third component comprises a catalyst; (b) evaporating at least some of a liquid in the homogenous solution after (a); (c) precipitating a first plurality of nanoparticles from the homogeneous solution in response to (a) or (b), wherein the first plurality of nanoparticles is formed on an inner surface of the vessel or in the homogeneous solution; (d) forming a first plurality of nanofins with the first plurality of nanoparticles, wherein the first plurality of nanofins is formed on the inner surface of the vessel with the first plurality of nanoparticles.

Embodiments described herein comprise a combination of features and advantages intended to address various shortcomings associated with certain prior devices, systems, and methods. The foregoing has outlined rather broadly the features and technical advantages of embodiments described herein in order that the detailed description that follows may be better understood. The various characteristics described above, as well as other features, will be readily apparent to those skilled in the art upon reading the following detailed description, and by referring to the accompanying drawings. It should be appreciated by those skilled in the art that the conception and the specific embodiments disclosed may be readily utilized as a basis for modifying or designing other structures for carrying out the same purposes of the embodiments described herein. It should also be realized by those skilled in the art that such equivalent constructions do not depart from the spirit and scope of embodiments described herein as set forth in the appended claims.

BRIEF DESCRIPTION OF THE DRAWINGS

For a detailed description of the preferred embodiments of the invention, reference will now be made to the accompanying drawings in which:

FIGS. 6A and 6B are graphical illustrations of the Raman Spectra for pure surfactants for materials fabricated according to embodiments disclosed herein.

FIGS. 7A and 7B are graphical illustrations of the Raman Spectra of SDS (Specimen II) for pre-DSC and post-DSC samples for materials fabricated according to embodiments disclosed herein.

FIGS. 8A and 8B are graphical illustrations of the Raman Spectra of SDBS (Specimen III) for pre-DSC and post-DSC samples fabricated according to embodiments disclosed herein and treated for four hours.

FIGS. 9A and 9B are graphical illustrations of the Raman Spectra of SDBS (Specimen III) for pre-DSC and post-DSC samples fabricated according to embodiments disclosed herein and treated for twenty-four hours.

DETAILED DESCRIPTION OF DISCLOSED EMBODIMENTS

Figure 1:
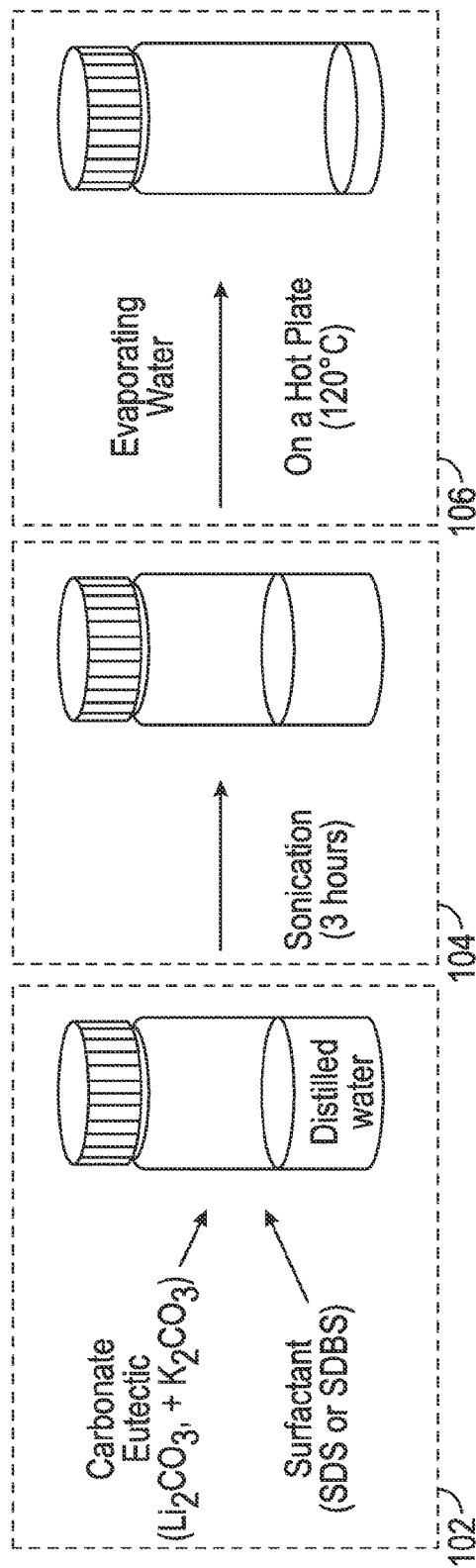
FIG. 1 is an embodiment of a method for preparing a sample according to certain embodiments disclosed herein.

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." As used herein, the term "nanofin" refers to a structure formed from a single nanoparticle or plurality of nanoparticles, the nanofin structures may act as and/or form nanogrooves or nanochannels on interior fluid transfer surfaces that may be curved or planar, or may otherwise act as transfer surfaces that aid in heat removal from a plurality of applications. In general, nanofins can define or form grooves or channels on surfaces of flow conduits or fluid containing vessels that may be curved or planar, or may otherwise act as enhanced heat transfer surfaces that aid in the removal of thermal energy across a plurality of applications. As used herein, the term "nanoparticle" refers to a particle with a size (at least one dimension, typically, the smallest dimension) or diameter less than 100 nm. In general, nanoparticles may have a variety of shapes including, without limitation, spherical, cubic, rectangular prismatic, pyramidal, cylindrical, irregularly shaped, or combinations thereof. As used herein, the term "nanofluid" refers to a mixture of liquid (e.g., solvent) and nanoparticles. In some embodiments, the liquid is doped with minute mass concentrations of nanoparticles (e.g., less than 5%). A "mass concentration," as used herein, may also be referred to a "concentration" or a "mass fraction" and may be defined as a mass of a dopant or other constituent divided by the total mass of the mixture in which the dopant or other constituent is disposed. Depending on the material composition and morphology of the particles, the optical properties and formation of nanofins and nanochannels as discussed herein may be perceptible for particle sizes, where at least one of the dimensions of the particle is in excess of 100 nm to include an average particle size of 100 nm-500 nm. In addition the particle lengths can be as high as 1000 nm-100,000 nm while the other dimensions of the nanoparticle is 100 nm-500 nm or from 1 nm-100 nm. As used herein, the term "optical property" refers to the interaction of a material with electro-magnetic waves for the entire electromagnetic spectrum as well as sub-atomic particles that can impinge on the material or can be generated within the material.

Since the industrial revolution remarkable advances have been achieved in science, engineering, and technology. Utilization of fossil-based energy resources has accelerated this growth. However, the fossil energy resources (such as petroleum, coal, and natural gas) are limited and have associated social costs due to emission of combustion byproducts. Advent of nuclear energy alleviated some of these issues but also resulted in another set of environmental issues—such as nuclear waste disposal, nuclear radiation leaks and thermal pollution. Consequently, the world is faced with the depletion of the energy resources and associated complications. For example, the combustion of fossil fuels has been perceived to cause several environmental problems such as global warming (carbon dioxide) and air pollution (nitrogen oxides or sulfur dioxide). Therefore, research on alternative energy resources such as renewable energy resources has garnered significant attention recently.

Solar energy, one of the renewable energy resources, is practically unlimited as well as environmentally clean. Solar energy can be harvested by photovoltaics (PV; direct method) or by concentrating solar power (CSP; indirect method). PVs use semiconductor materials to directly convert the solar energy (radiant light) to electricity. CSP uses solar receivers (mirrors or lenses) to concentrate the solar energy (thermal energy), and the concentrated thermal energy is typically converted to electricity using thermodynamic cycles (e.g., supercritical cycles, Rankine cycle or Stirling cycle). Thermal energy storage (TES) enables the continuous production and supply of electricity derived from solar energy during cloud cover or during nighttime. Materials used for thermal energy storage may allow excess thermal energy to be collected for later use, for example, balancing energy between seasons and/or between times of day.

Molten salts can be alkali-nitrate, alkali-carbonate, alkali-chloride (or halogen derivatives), or eutectic mixtures of these salts. Such molten salts have a wide range of melting points from about room temperature to about 600° C., and some of the salt formulations are generally stable up to about 1600° C. Using such molten salts as materials for TES confer several potential benefits including: (1) the high temperature stability of the molten salts can increase the operating temperature of the CSP, and thus, enhance the thermodynamic cycle efficiency; (2) the molten salts are often lower cost than conventional TES materials, and thus, the system costs of the CSP can be reduced significantly; and (3) the molten salts are environmentally safe (both in their use and procurement/synthesis), especially as compared to most conventional TES materials (e.g., thermoplastics, cement and concrete). Hence, utilizing molten salts for TES can obviate or reduce the potential costs for environmental remediation in power generation applications. Molten salts are a subset of fluids called "ionic liquids" in which the liquid phase of these materials are known to dissociate into ions or species that carry electrical charge. Hence, embodiments and claims described here can also be applied to other types of ionic liquids. Other fluids that do not dissociate into ions are termed as "polar liquids" which encompass materials such as water, as well as materials which are composed of alternate chemical structures (such as covalent bonds or hydrogen bonding interactions). The embodiments and claims described herein can also be applied to other types of polar liquids. However, the limited range of thermal and optical properties such as optical transmissivity, optical absorptivity, radiation cross-section (for nuclear reactions and absorptivity), thermal expansion coefficient, specific heat capacity and thermal conductivity, as well as ionic conductivity of the liquid phase of these materials may present challenges for some applications in thermal management, energy conversion, power generation and TES. In some embodiments, a catalyst may be used in addition to at least one of the molten salt and/or the surfactant. The catalyst can comprise, for example, a polyelectrolyte complex nanoparticle (PCN) such as polyethylenimine Solid particles with desirable thermo-physical properties can be added to liquid solvents to effectively enhance the overall thermo-physical and optical properties of the liquid mixture. However, the stability of the mixture has often been a source of concern, since some solid particles have a propensity to agglomerate in the liquid or precipitate from the liquid suspension as a result of agglomeration. Liquids doped with nanoparticles (e.g., to enhance thermo-physical properties) are often referred to as "nanofluids" as discussed above. Since nanometer-sized particles ("nanoparticles") have very large surface area to volume ratios, the surface energy of the nanoparticle is significantly higher as compared to micrometer- or millimeter-sized particles. The increased surface energy enables a nanoparticle to achieve stable dispersion in the liquid, thereby enhancing the stability of the resulting mixture. Hence, stable suspensions comprised of nanoparticles mixed with solvents can be realized by following suitable synthesis techniques. This concept may also be applicable in solids, where dispersed nanoparticles in a matrix (solid phase) are termed as "nanocomposites."

Typical examples of high heat flux devices include integrated circuit (IC) chips for electrical/computational applications, optical devices (e.g., cutting and manufacturing using high power lasers), and advanced energy storage systems (e.g., high temperature thermal storage, batteries and fuel cells). These devices often experience significantly high thermal loads due to their relatively small size (i.e., less surface area available for cooling) and relatively high thermal energy generation. The thermal energy generation can be quantified as volumetric heat generation (i.e., heat generation in a device per unit volume of the device) or specific heat generation (i.e., heat generation within an object per unit mass of the object). Non-uniformity in the temperature distribution within these devices, typically due to inefficient cooling, leads to formation of localized "hot-spots" that can negatively affect reliability, device lifespan and operational speeds. Thus, the development of improved cooling systems and methods for efficient thermal management of these high heat flux devices is desirable for many applications.

Conventional approaches to improving the cooling efficiency of thermal management platforms in single phase flows have focused on enhancing the thermal properties of the heat transfer media (i.e. the coolant) or by increasing the effective surface area available for transferring thermal energy on heat exchanging surfaces. The experiments described herein address a variety of goals including the development of nano-scale temperature metrology platform. The nano-scale metrology platforms can be used for monitoring thermal energy exchange between different components, such as the convective heat transfer phenomena of simple (Newtonian) fluids and complex fluids (nanofluids). Such goals include the design, fabrication, testing, calibration and deployment of high quality sensors which can range in dimensions from millimeter size to size of atoms and molecules. Such miniaturized sensors (can be utilized to measure temperature of coolants in microchannels, while minimizing the perturbation of the transport mechanisms under investigation.

One example of temperature nano-sensors is the Thin Film Thermocouple (TFT) which is realized by the deposition of two dissimilar materials, which cause the generation of electrical potential (due to Seebeck effect) arising from the temperature differential between the junctions of the two materials in contact. Typically, the TFT nano-sensors can be realized to a thickness of 200-400 nm and any such temperature metrology devices smaller than this length scale can lose their efficacy for temperature measurement. Conventional thermocouples are realized by joining the wires of two different materials (e.g., Chromel and Alumel). Another example of temperature nano-sensors is the Diode Temperature Sensor (DTS). In DTS, semiconductor materials behave as diodes allowing preferential flow of electrical charge in a particular direction depending on the chemical composition of the semi-conductor material. The flow of electrical charge (i.e., electrical current) at a particular location in the semi-conductor material is proportional to the temperature at the location and therefore the measurement of electrical current can be used to estimate the temperature of the material. This measurement technique can be used to realize temperature nano-sensors which can be in the size range of 1 nm-1 mm. However, TFT are passive devices and do not require external power sources for measurement. In contrast, DTS are active devices and can require external power sources for efficient operation which can also lead to local thermal perturbation due to the act of measuring the temperature. In contrast to conventional methods of manufacturing and using nanofluids, the nanofluids disclosed herein are formed using at least one component, for example, an aqueous component, that does not have nanoparticles added to it, but rather forms nano-particles in-situ, which may then form nanofins. Such nanofins may form channels or grooves that assist with thermal energy storage, chemical reactions (e.g., thermo-chemical energy storage), catalysis, energy harvesting, power generation, thermal management, and heat removal. The heat removal can be due to the physical and chemical interaction of the nanoparticles with the fluids, for example, by increasing the effective surface area available for inter-molecular interactions that can aid in transport mechanisms such as for energy, mass, and species transport.

In one embodiment, discussed in detail below, nanoparticles are synthesized in-situ by adding a surfactant to a molten salt. The nanoparticles can be formed upon the combination of the two components, when the mixture becomes homogenous, when the liquid is evaporated from the aqueous solution, or combinations thereof. The nanoparticles precipitate in the solution itself and/or on the walls of the vessel where the components are combined. The precipitation of nanoparticles forms a nanofluid. In some embodiments, a removable substrate is placed in the vessel prior to the addition of one or both components. This substrate can be of any geometry suitable for an application where nanofins are desirable. The nanoparticles can form nanofins on the substrate and/or on at least a portion of the vessel. In general, a vessel may be a closed container, a container open in one location, or a container open in more than one location (e.g., a fluid conduit or pipe). The nanoparticles can form nanofins on the substrate or inside the vessel either by the nanoparticles forming on those surfaces and in some cases, instead of or in addition to this formation, the nanoparticles that form in the solution may attach to other nanoparticles that may be in the solution or on a surface to form nanofins. A collection of nanofins define nanogrooves or nanochannels, which may also be described as microchannels. Thus, as used herein, the term "microchannel" refers to a small channel and includes, without limitation, features or a plurality of features that are formed using the methods discussed herein; it may also refer to an existing feature that may or may not have been formed according to embodiments of the present disclosure which the nanoparticles formed in-situ as disclosed herein may form on and/or inside of.

In an alternate embodiment, only a surfactant in aqueous form is used to form the nanoparticles. The surfactant is heated in the vessel or prior to being disposed in the vessel, and precipitates nanoparticles that also form nanofins and nanogrooves as discussed above. In some embodiments, nanoparticles are formed in-situ as described above using either a surfactant or a molten salt and a surfactant resulting in the formation of nanoparticles suspended in the liquid (i.e., a nanofluid). For the nanoparticles that are formed in-situ, the process can be halted while there are nanoparticles in the fluid and that may not have formed nanofins yet. In some embodiments, this is accomplished without evaporating at least a portion of the liquid. This type of synthesis of nanoparticles can be performed using alternate techniques by one skilled in the art such as synthesis of nanoparticles by self-assembly at material interfaces. The nanofluid may then be introduced to other environments to form nanofins and nanogrooves or nanochannels as discussed in detail below.

In embodiments described herein, nanofins can be formed from nanoparticles in-situ, i.e. formed in the vessel in which the reacting material or materials are disposed. This differs from conventional methods where nanoparticles formed in a previous process are introduced to a chosen environment. Using embodiments of systems and methods discussed herein, the fluid containing surfaces, pipes, conduits, wafers, and other surfaces can include microchannels formed from nanofins, and re-formed. Re-forming may occur if, for example, a plurality of nanofins are formed from a first material and then the same vessel, for example, a pipe, is to be used to transfer a different type of material that may be more responsive to heat removal if a different type of nanoparticle is formed in-situ. In that case, the pipe may be cleaned out, for example, with water, organic solvents, an acid or a base, and the plurality of nanoparticles and nanofins re-formed. In contrast, if the same pipe had interior channels formed by reaming or other machining, there may be integrity issues introduced by reaming out that surface and re-forming the grooves mechanically. These additional processing steps, such as reaming or re-forming, can also add to the cost while in contrast flowing nanofluids in the same pipe interior can be used to achieve nano-scale roughness due to precipitation of the nanoparticles—thus resulting in enhanced transport of heat (thermal energy), mass and chemical species (e.g., diffusion) for the same magnitude of forcing agent, such as pressure drop, electrical potential or chemical potential difference. Excessive precipitation of nanoparticles can be utilized to realize opposite behavior—i.e., decrease in transport of heat (thermal energy), mass and chemical species (e.g., diffusion) for the same electrical potential or chemical potential difference. Hence, nanofluids (or nanoparticle suspensions) can be used to realize tunable properties—such as thermal, rheological, nuclear cross section (e.g., for absorptivity) and optical behavior.

The particle sizes of the nanoparticles dispersed in these nanofluids may be, in some embodiments, from about 1 nm to about 100 nm or, in other embodiments, greater than about 100 nm. The particle size may depend on the end application, the vessel type, the vessel material, the gas and/or fluid flow pattern and/or composition, as well as the vessel geometry. In an embodiment, the uniform dispersions may be obtained at mass concentrations below about 5%. For certain types of nanoparticles it is possible that these embodiments can be realized for mass concentration of nanoparticles exceeding 5% to 50%. In addition, the experiments discussed herein may utilize nano-fabrication techniques. An embodiment of these nano-fabrication techniques is the Step and Flash Imprinting Lithography (SFIL). The nano-fabrication techniques can be used for obtaining surface nanostructures (nanofins, nanochannels). The surface nano-structures can be used to enhance the surface area for augmenting energy transfer (thermal, optical, nuclear, etc.) and mass transfer. These surface nanostructures can be used to evaluate the contribution of various parameters such as variation in nanoparticle concentration values, variation in nanoparticle material composition, variation in nanoparticle morphology, geometry of the nanofins and nanochannels, variations in the material composition of the nanofins and nanochannels, wall temperature, and flow velocity on the thermal energy transfer characteristics of nanofluid materials during flow in a nanochannel (microchannel).

In addition, the experiments discussed herein address the effect of surface nano-structures ("nanofins") on heat transfer and correlate the behavior with the thermal efficacy of nanofluids flowing in a microchannel (i.e., prove that nanoparticle precipitates from nanofluids can act as "nanofins"). Hence, this can help prove that the surface interactions are more dominant in determining the thermal efficacy of nanofluids than their bulk property values. The disclosure may further demonstrate the feasibility of non-contact temperature metrology techniques for experimental flow visualization and heat transfer measurements (especially in the near wall region) using quantum dots (QDs) and laser-induced-fluorescence (LIF) techniques, and demonstrate the feasibility of using this experimental platform combining flow boiling, microchannels, nanofluids and integrated nanosensor array.

Specific heat capacity enhancements of carbonate salts of different mixture ratios (which were then mixed with surfactants) were obtained from DSC experiments. In one embodiment, the experiments were performed for two different surfactants sodium dodecyl sulfate (SDS) and sodium docedylbenzenesulfonate (SDBS). In-situ synthesis of carbon nanoparticles were demonstrated in these studies. In-situ synthesis of carbon nanoparticles in these eutectic salt samples was accompanied by significant enhancement of the specific heat capacity of these samples. Materials characterization experiments were performed using laboratory instruments and techniques such as Raman Spectroscopy, and electron microscopy. The electron microscopy visualization techniques used for verification include Tunneling Electron Microscopy (TEM) and Scanning Electron Microscopy (SEM). Also, elemental composition analyses were performed using Energy Dispersive X-Ray Spectroscopy which is also called Energy Dispersive Spectroscopy (EDS). Thermal property measurements for specific heat capacity was performed using ASTM protocol 1839 using Differential Scanning Calorimetry (DSC). These experiments demonstrate at least:

(a) Enhancement of specific heat capacity exceeded 18% by adding organic surfactants at mass concentration of 0.5% and 1% to carbonate salt mixtures at eutectic composition. This enhancement values are comparable with the experimental measurements for the nanomaterials that were synthesized by explicitly mixing nanoparticles (that were pre-formed) with pure salt mixtures.

(b) The increase in the amount of surfactants (to mass concentration of 5%) leads to a decrease in the specific heat capacity of the salt-surfactant mixtures. Additionally, huge degradation in the specific heat capacity values were observed for the Specimen II samples (salt-SDS mixture) in successive cycles during the thermocycling experiments performed in the DSC apparatus. Repeated heating and cooling of the samples is termed as thermocycling. Often thermocycling can involve repeated melting and solidification or repeated evaporation and condensation of the materials in the samples, particularly the solvent material.

(c) It was found that the duration of heating during the dehydration step (for sample preparation) may affect the specific heat capacity enhancement for salt-SDBS mixtures. While there was no enhancement of the specific heat capacity for the Specimen III samples heated for the short periods (less than 4 hrs. at 120° C.), the Specimen III samples which were heated for extended periods (about 24 hrs.) showed significant enhancement of specific heat capacity values.

(d) The Raman Spectra for the Specimen III samples—for both pre-DSC and post-DSC samples—demonstrated the existence of carbon nanoparticles.

(e) The nanoparticles that were formed in-situ in these experiments were visualized using TEM.

(f) Elemental composition analyses using EDS conclusively showed that carbon nanoparticles were formed in-situ in these experiments.

Experimental procedure—Control experiments were performed to estimate the contribution of the surfactants utilized for homogeneous dispersion during sample preparation—to the total specific heat capacity of the nanomaterial samples. Several types of organic surfactants such as sodium dodecyl sulfate (SDS) and sodium docedylbenzenesulfonate (SDBS) were used to improve the uniformity of nanoparticle dispersion in water. As a consequence of homogeneous dispersion—unagglomerated nanoparticles were obtained in the nanomaterials with a concomitant enhancement in the specific heat capacity values of the nanomaterials. To ascertain the contribution of the surfactant material to the total specific heat capacity of the nanomaterials, control experiments were designed and implemented. In the control experiments, a plurality of pure salt mixtures, which may be referred to as "molten salt," were doped with the same mass fraction of the surfactants but without nanoparticles. This is in contrast to the conventional method of forming a nanofluid where pre-formed nanoparticles are introduced into an aqueous solution of one or more component. The specific heat capacity values of these salt samples were measured. It was observed that the level of enhancements for salt samples with surfactants were typically much higher than for salt samples with surfactants in which nanoparticles were also added to the mixture.

Materials characterization of these samples with surfactants but without the addition of nanoparticles to the mixture demonstrated the formation of organic nanoparticles, which may have resulted from chemical degradation of the surfactants themselves. Materials characterization techniques involved micro-Raman Spectroscopy (mRS) and Tunneling Electron Microscopy (TEM). These nanoparticles that were formed in-situ during the thermocycling experiments (repeated melting and solidification of the samples) performed using the samples of molten salt mixtures containing surfactant only resulted in higher levels of enhancement as compared to samples where nanoparticles were added during the sample preparation step.

Sample preparation—FIG. 1 illustrates an embodiment of a sample preparation method in accordance with the principles described herein. At block 102, a base material (solvent) is formed, composed of the eutectic composition of a carbonate salt mixture, for example, $Li_2CO_3+K_2CO_3$. Also at block 102, at least one surfactant, for example, sodium dodecyl sulfate (SDS) or sodium docedylbenzenesulfonate (SDBS) is homogeneously dispersed into the aqueous solution of the pure salt mixture. At block 104, the homogenous mixture undergoes sonication for a period of time, for example, for about 3 hours. At block 106, the sonication at block 104 is followed by complete/substantial dehydration of the sample. FIG. 1 shows the sample preparation for the salt-surfactant mixtures. In the water evaporation step at block 106, a hotplate may be used. In one example, the hotplate temperature was set to about 120° C. and the aqueous solution remained at this temperature until substantially all of the aqueous solution had evaporated. The aqueous solution may be deposited on to the hotplate in a single transfer, or may be deposited drop by drop or in another method depending upon the composition of the solution. In some examples, the hotplate temperature may be set up to 250° C. for rapid evaporation of water. In an alternative embodiment, rapid water evaporation or "flash evaporation" could also be achieved by connecting the container to a vacuum pump or an evacuated chamber which could enable the formation of a homogeneous mixture with nanoparticles formed in-situ.

A Raman spectrometer (Model: Horiba Jobin-Yvon LabRam IR) was used to confirm the existence of carbon nanoparticles in the samples by scanning changes in chemical structures of the surfactants. Raman measurements were performed with powder samples of the salt-surfactant mixtures—both before and after the experiments. He—Ne laser (632 nm) was chosen as a light source for optical excitation of the samples. The spectrometer is equipped with a charge coupled detector device (CCD) cooled by liquid nitrogen. The spectral resolution was about 0.16 cm$^{-1}$ for the experimental conditions used in this study.

Three sample groups were prepared using a method similar to the method in FIG. 1:

Specimen I: pure surfactants—both SDS and SDBS;
Specimen II: surfactant (SDS) mixed with eutectic salt mixture; and
Specimen III: surfactant (SDBS) mixed with eutectic salt mixture, where, for the dehydration step, different samples of this specimen were subjected to either short duration heating or longer duration heating. Specimen I was pure surfactant and was used as received. The sample preparation protocol for Specimen II and Specimen III involved the preparation of an aqueous solution of the surfactants mixed with the eutectic salt followed by dehydration on a hotplate at 120° C. to obtain the dry powder of the nanomaterial samples. For Specimen II the dehydration step was limited to 4 hours. For Specimen III, the dehydration step was fixed at 4 hours for one set of experiments and 24 hours for another set of experiments.

Specific heat capacity measurement experiments. The experimental procedure for the DSC experiments comprises thermocycling involving repeated melting-solidification of the samples and calculation procedure for estimating the specific heat capacity of the samples. This thermocycling may comprise individual cycles and/or an overall cycle from about one microsecond to twenty-four hours, from one day to three months, and from three months to a year. The effect of the water evaporation step on the specific heat capacity was explored for the salt-SDBS mixtures. For some of the samples, dehydration was performed for 4 hours. However, for some of the other samples the dehydration step was continued for 24 hours. In other embodiments, a dehydration/drying time can vary from five minutes to more than twenty-four hours, and in yet further embodiments, a dehydration/drying time may vary from 1 microsecond to twenty-four hours, or from one day to three months, or from three months to a year.

To ensure the reliability of the Raman Spectra measurements the results for the Specimen I were compared with the reference data provided by the manufacturer (Sigma-Aldrich) and were found to be consistent. Subsequently, Raman Spectra measurements for salt samples mixed with surfactants (Specimen II and Specimen III) were performed. The differences in the Raman Spectra measurements for the two specimens were then evaluated. Appearance of additional peaks like a carbon-carbon bonding in Specimens II and III were used to prove the existence (or formation) of carbon nanoparticles (i.e., graphitic nanoparticles).

Transmission Electron Microscope (TEM; Model: JEOL, JEM-2010) equipped with Atmospheric Thin Window (ATW) type Energy Dispersive Spectroscopy (EDS) detector (Oxford Instruments) was employed as an independent alternative method to verify the formation of carbon nanoparticles in Specimen III. Using the TEM images and EDS results, existence of carbon nanoparticles were ascertained in the post-DSC samples. EDS spectra for the nanoparticles on silicon monoxide grids were measured to confirm that the observed nanoparticles in the TEM images were indeed due to carbon-carbon bonding, which proved the formation of carbon nanoparticles from the chemical degradation of the surfactant molecules.

Figure 2:
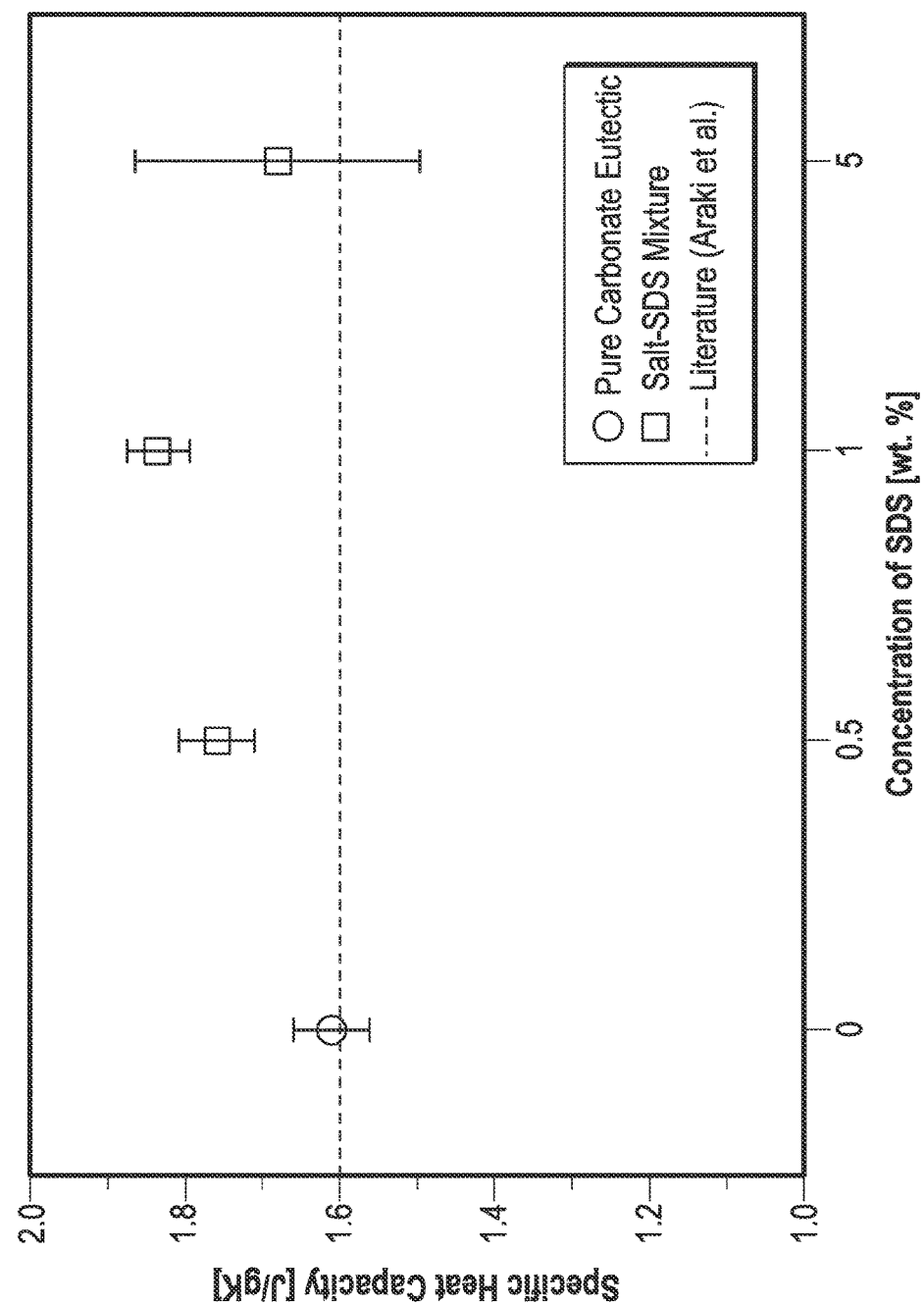
FIG. 2 is a graphical illustration of specific heat capacity values as a function of SDS concentrations according to embodiments disclosed herein.

Results and discussion—Specific heat capacity of eutectic-SDS mixtures—FIG. 2 illustrates specific heat capacity values according to embodiments of the present disclosure. FIG. 2 shows the specific heat capacity values of the carbonate salt eutectic-SDS mixtures for three different mass concentrations of SDS, 0.5%, 1.0%, and 1.5%. Compared to the specific heat capacity of the pure salt eutectic, which is comprised of SDS at mass concentration of 0%, the specific heat capacity values were significantly enhanced in the samples containing SDS. The enhancement of the specific heat capacity for the sample prepared using SDS at 0.5% mass concentration was about 11.6%. With increase in the mass concentration of SDS from 0.5% to 1%, the specific heat capacity of the mixture was increased from 1.761 [J/g·K] to 1.836 [J/g·K], which corresponds to an enhancement ranging from 11.6% to 16.3%, respectively. For the sample prepared using SDS at a mass concentration of 5%, however, the specific heat capacity was decreased to 1.659 [J/g·K], which leads to the conclusion that there was no enhancement since the level of enhancement in this measurement was within the margins of the measurement uncertainty.

Figure 3A:
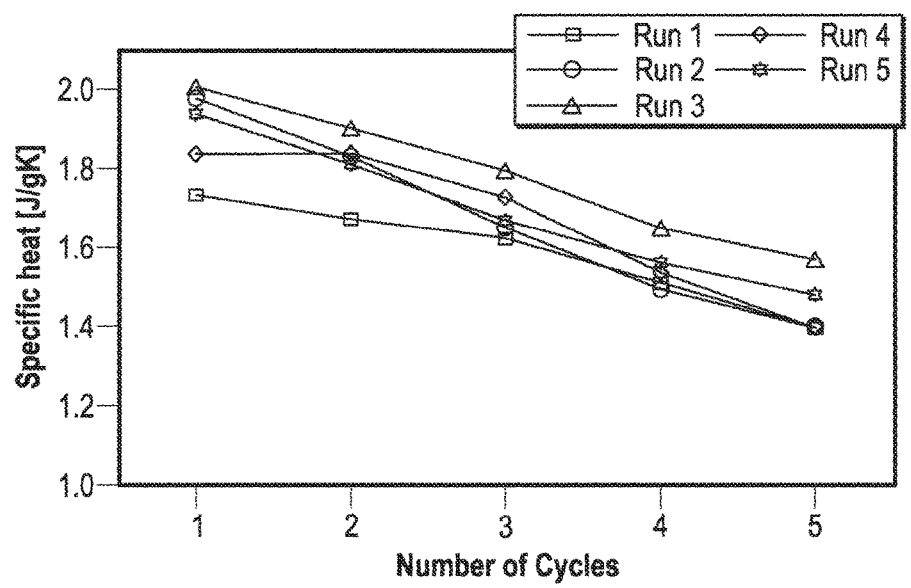
FIGS. 3A-3F are graphical illustrations of specific heat capacity values for samples with various sodium dodecyl sulfate (SDS) mass concentrations for materials fabricated according to embodiments disclosed herein.
Figure 3B:
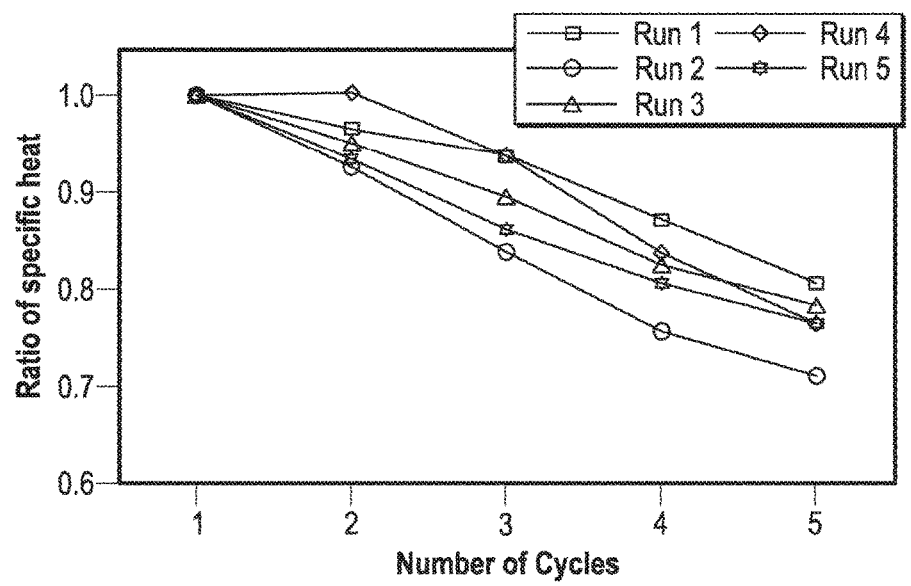
Figure 3C:
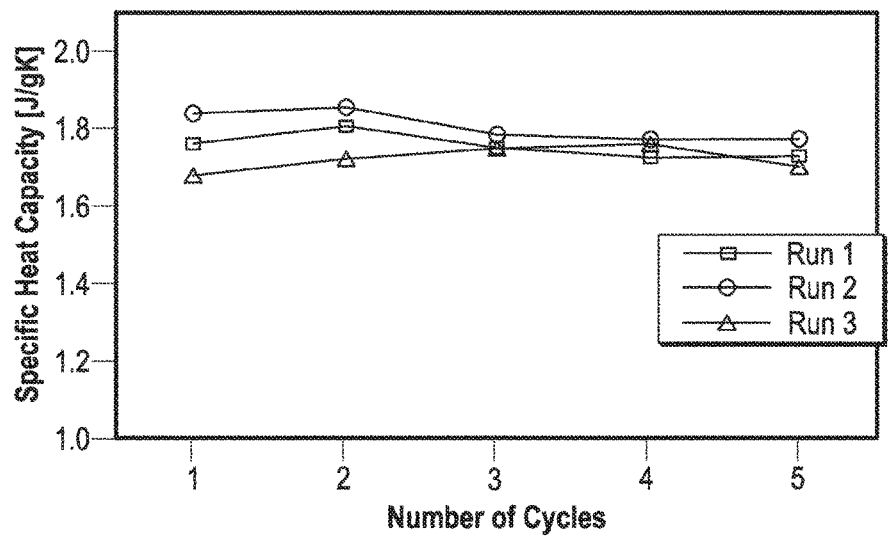
Figure 3D:
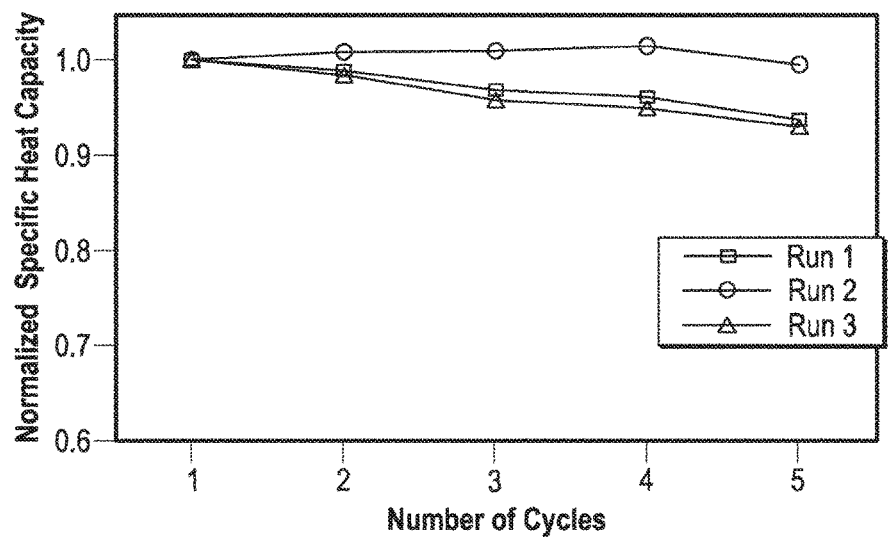
Figure 3E:
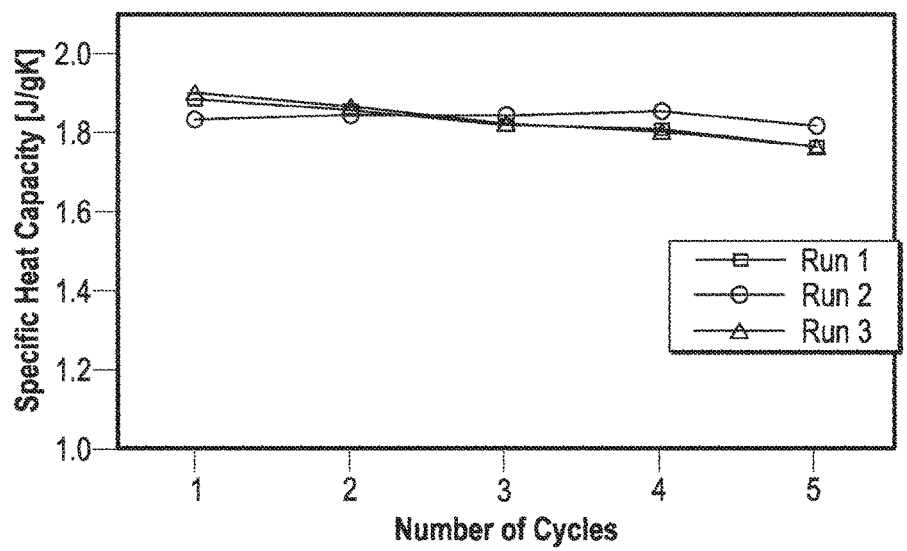
Figure 3F:
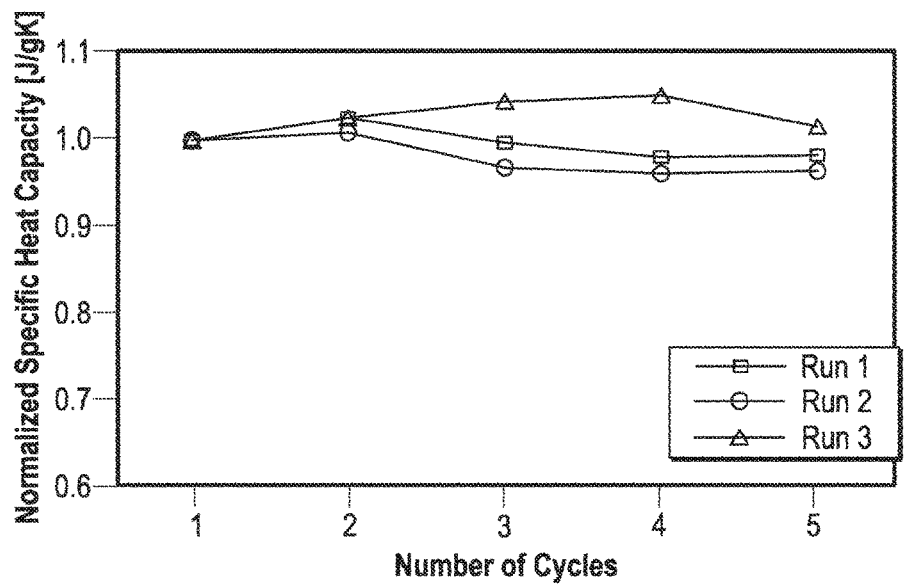

FIGS. 3A and 3B illustrate the specific heat capacity values for samples mixed with SDS at mass concentration of 5%. The progressive degradation in the measured values for successive cycles for the different experiments that were conducted on different days are indicated by the different runs. FIG. 3A shows the plots with original values of the specific heat capacity measurements obtained from these experiments. The normalized values of the specific heat capacity (normalized to the first value obtained in successive thermocycles) are shown in FIG. 3B. As shown in the figures, the huge degradation of the specific heat capacity of the samples (SDS mixed at mass concentration of 5%) was observed. The degradation in the final value (compared to the first value) was as much as 34%. For some of the other samples containing SDS at lower values of mass concentrations, however, almost uniform values of specific heat capacity were obtained from the successive cycles in each thermocycling experiment. FIGS. 3C-3F illustrate the specific head capacity values for samples mixed with SDS at mass concentrations of 1.0% and 0.5%. FIGS. 3C and 3D illustrate, respectively, the specific heat capacity and the normalized specific head capacity for samples with a mass concentration of SDS of 0.5%. FIGS. 3E and 3F illustrate, respectively, the specific heat capacity and the normalized specific head capacity for samples with a mass concentration of SDS of 1.0%. The measured values of the specific heat capacity were within 98% and 93% of the first value, respectively.

From the enhanced specific heat capacity values measured in the DSC experiments and the anomalous variation in specific heat capacity with variation mass concentration of SDS in the salt samples, it may be said that the thermocycling (repeated melting and solidification of the salt samples) induced changes in the chemical structure of SDS. The thermocycling experiments involved operation at high temperatures ranging from 150° C. to 560° C., and comprised a repeated heating and cooling cycle that resulted in at least partial melting and solidification. The carbon chains of SDS which were attached to sulfate groups were potentially disrupted at these high temperature conditions leading to consolidation of the carbon-carbon bonds to form carbon (e.g., graphite) nanoparticles. As mentioned before, doping carbonate salt mixtures (including eutectic) with small amounts of organic nanoparticles resulted in enhancement of the specific heat capacity of the salt mixtures. Therefore, the carbon nanoparticles formed in-situ in these thermocycling experiments are also expected to enhance the specific heat capacity values of the resulting nanomaterials (even though the samples did not contain any nanoparticles to begin with during the sample preparation step).

Figure 4:
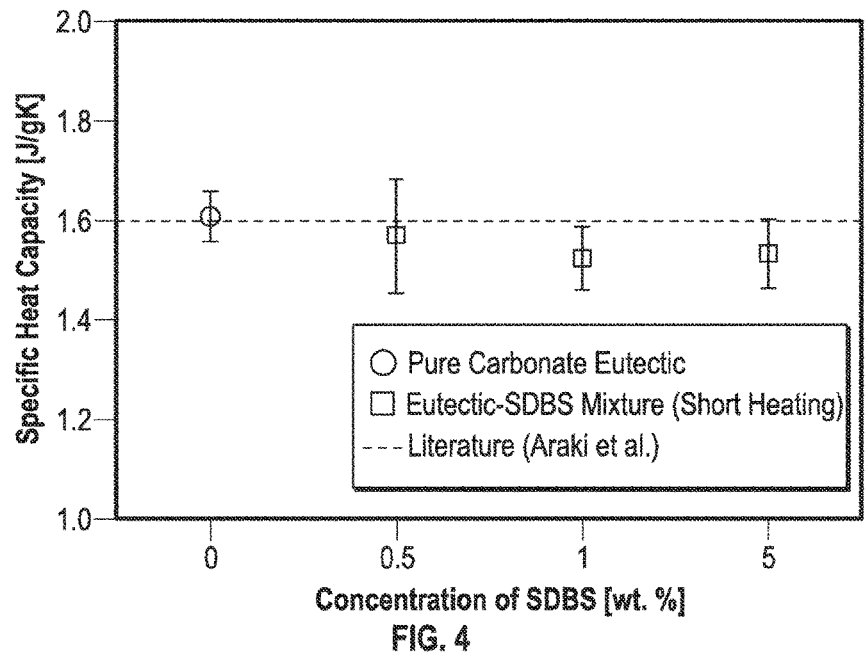
FIG. 4 is a graphical illustration of specific heat capacity values as a function of sodium docedylbenzenesulfonate (SDBS) mass concentrations according to embodiments disclosed herein.

Specific heat capacity of eutectic-SDBS mixtures. FIG. 4 illustrates specific heat capacity values according to embodiments described herein. Another organic surfactant, SDBS, was used to verify whether the same technique can be used for other surfactant materials. FIG. 4 illustrates the specific heat capacity of samples with mass concentration of SDBS of 0.0%, 0.5%, 1.0%, and 1.5%. The liquid-phase specific heat capacity of salt eutectic-SDBS mixture was measured. The same protocol was employed to prepare the mixtures, and experimental conditions were also the same as salt-SDS mixtures. FIG. 4 shows the specific heat capacity of the salt-SDBS mixtures as a function of the SDBS mass concentration. Surprisingly, the specific heat capacity was not enhanced by adding SDBS in the carbonate salt eutectic, and rather was marginally degraded compared to that of the pure eutectic sample. The increase in the concentration of SDBS did not significantly affect the specific heat capacity of the mixtures. This discrepancy in behavior for the samples mixed with the two different surfactants (SDS and SDBS) may be explained by the fact that there is a large difference in the decomposition temperature for SDBS compared to that of SDS. As reported in previous studies, SDS is easily decomposed by prolonged heating at over 40° C. On the other hand, the decomposition temperature of SDBS is known to exceed 238° C.

Figure 5:
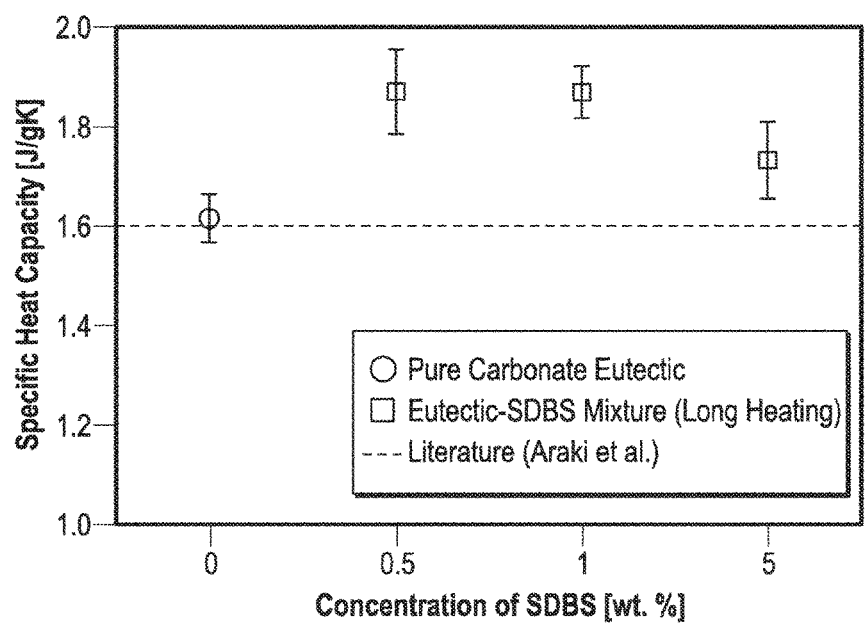
FIG. 5 is a graphical illustration of the specific heat capacity values of samples containing SDBS surfactant fabricated according to embodiments disclosed herein and that were heated for a longer duration than the samples analyzed in FIG. 4.

Hence, to cause chemical decomposition of SDBS, prolonged heating of the samples containing SDBS at elevated temperatures may be employed. Therefore, the salt-SDBS mixtures were heated for additional durations even after the complete dehydration of the salts-SDBS water solution was achieved. The heating duration of the salt-SDBS mixtures was prolonged to 24 hours at 120° C. FIG. 5 illustrates the specific heat capacity values of these samples containing SDBS surfactant that were heated for a longer duration than the samples in FIG. 4. In contrast to the samples heated for shorter duration in FIG. 4, the specific heat capacity of the SDBS samples in FIG. 5 was significantly enhanced for all mass concentrations of SDBS for the samples with prolonged heating during the dehydration step. For the samples with prolonged thermal treatment during dehydration step, in particular those samples containing SDBS at mass concentration of 0.5% and 1%), the specific heat capacity enhancement exceeded about 18% as compared to that of the pure salt mixture samples. Interestingly, the specific heat capacity for the samples subjected to prolonged heat treatment during dehydration step (containing SDBS at mass concentration of 5%) was lower than the samples containing SDBS at lower mass concentrations. Nevertheless, there was no significant degradation in the specific heat capacity values for successive cycles during thermocycling experiments for this sample.

Trace of carbon nanoparticles: Raman spectrum—As mentioned in the Experiments subsection above [0047], Raman Spectra were obtained for the three different sample groups: (1) Specimen I (pure surfactants SDS and SDBS, used as received), (2) Specimen II (eutectic salt mixed with SDS, dehydrated at 120° C. for 4 hours), and (3) Specimen III (eutectic salt mixed with SDBS, dehydrated at 120° C. for 4 hours or 24 hours). As indicated, each sample group was composed of salt mixtures with surfactants at different mass concentrations ranging from 0-1.5% and the process parameters (such as time for dehydration of the samples) were also varied.

FIGS. 6A and 6B illustrate Raman Spectra for pure surfactants. FIG. 6A illustrates the results for pure SDS sample and FIG. 6B illustrates the results for pure SDBS sample, which are described as Specimen I in [0039]. The spectrum of the two surfactants were compared with the reference spectra provided by the manufacturer (Sigma-Aldrich). The measured spectra for the samples were found to be consistent with spectra supplied by the manufacturer. This confirms the reliability of the measurements and the purity of the as-received surfactant samples. The Raman spectrum of pure SDS in FIG. 6A consists of sharp peaks at around 2900 $cm^{-1}$ and several week peaks at around 1450 $cm^{-1}$, 1300 $cm^{-1}$, 1130 $cm^{-1}$, and 1175 $cm^{-1}$, including peaks that occurred in shoulder regions of the other peaks. The spectrum of pure SDBS shows a series of peaks located at around 2900 $cm^{-1}$ and a relatively weak peak at 3060 $cm^{-1}$. It also includes some sharp and weak peaks between 1600 $cm^{-1}$ and 500 $cm^{-1}$. These measurements were performed to confirm the manufacturer's data, the reliability of the measurements and were consistent with the manufacturer's data for Raman Spectra for these surfactants.

FIGS. 7A and 7B show the Raman Spectra of SDS (Specimen II) for pre-DSC and post-DSC samples. Prior to measuring Raman spectra of Specimen III (salts-surfactant mixtures), Raman spectra of pre-DSC and post-DSC samples were measured for Specimen II in order to examine the occurrence (or absence) of specific peaks in the spectra—both before and after the thermocycling experiments were performed using the samples in a DSC. Comparing FIG. 7A with FIG. 6A, the Raman spectrum of the pre-DSC SDS sample (Specimen II) appeared to be similar to the spectrum of Specimen I, as shown in FIG. 6A In other words, there is no significant difference between pure SDS samples (Specimen I) and pre-DSC samples (Specimen II). However, the Raman spectra in FIG. 7B were obtained from the post-DSC sample was entirely different from the pre-DSC sample in FIG. 7A, where two main features were observed in the Raman spectrum measurements. As shown in FIG. 7B, most of the peaks observed in the pre-DSC samples in FIG. 7A vanished and two broad-band peaks at 1566 $cm^{-1}$ and 1335 $cm^{-1}$ appeared for the post-DSC sample. The Raman shifts of 1566 $cm^{-1}$ and 1335 $cm^{-1}$ are in accordance with G band and D band in carbon structures such as carbon nanotubes and graphite nanoparticle. From the Raman Spectra measurements of Specimen II, it can be deduced that the surfactants were decomposed due to the high temperature condition in the DSC and that carbon atoms of the surfactants spontaneously formed carbon nanoparticles during the DSC experiments.

FIGS. 8A and 8B illustrate the Raman Spectra of SDBS (Specimen III) for pre-DSC and post-DSC samples treated for four hours. Finally, Raman spectra for the Specimen III samples were also obtained in this study. The results for both salt-SDS mixtures and salt-SDBS mixtures are shown in FIGS. 8A and 8B. FIGS. 9A and 9B illustrate the Raman Spectra of SDBS (Specimen III) for pre-DSC and post-DSC samples treated for twenty-four hours. For the pre-DSC samples (Specimen III), most of the peaks in Raman Spectra were observed to have disappeared except for two peaks located between 1000 $cm^{-1}$ and 1150 $cm^{-1}$. From this result it can be expected that the chemical structures may have changed during sample preparation (e.g. during dehydration step). FIG. 8B and FIG. 9B show Raman spectra for the post-DSC samples for the two mixtures of the 4-hr and 24-hr SDBS specimens. Surprisingly, in FIG. 7B, the G 704 and D 702 band peaks were observed in the Raman Spectra (at 1592 $cm^{-1}$ and 1323 $cm^{-1}$). Consistent with the Raman Spectra observed for the Specimen II samples, the same peaks were also obtained as seen in FIG. 9B for the Specimen III samples (eutectic salt-SDBS mixture); however the G 904 band and D 902 band peaks were slightly shifted to 1556 $cm^{-1}$ and 1321 $cm^{-1}$.

Hence the Raman Spectra measurements conclusively proved the formation of carbon nanoparticles in this study. However, there were small differences in the peaks observed in the Raman Spectra for the position for G band (704, 904) and D (702, 902) band for the Specimen II (FIG. 7B) and Specimen III (FIG. 9B) samples. The shift in the location of the peaks in the Raman Spectra may be explained by the variation of the extent of structural disorder and clustering of lattice atoms of the nanoparticles formed in-situ in the two samples.

Figure 10A:
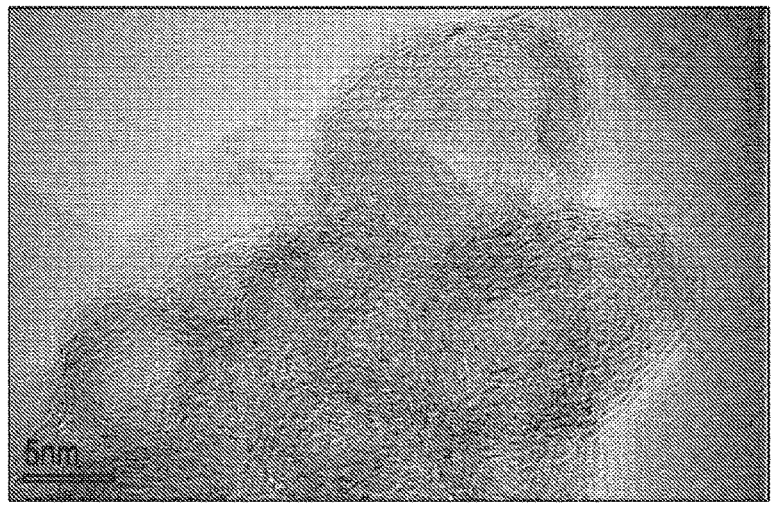
FIGS. 10A and 10B are TEM images of samples fabricated according to embodiments disclosed herein.
Figure 10B:
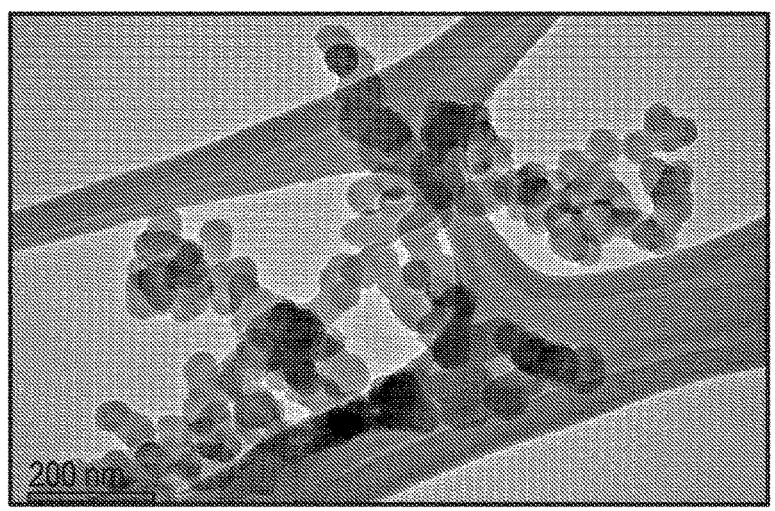

FIGS. 10A and 10B are TEM images of samples manufactured according to embodiments of the present disclosure. Trace of carbon nanoparticles: Transmission electron microscope (TEM)—Using Raman spectroscopy, the existence of the carbon nanoparticles in the salt-surfactant mixtures (post-DSC samples) was established. TEM measurements were performed to determine the size of the nanoparticles formed in-situ. FIGS. 10A and 10B shows electron microscopy images of carbon nanoparticles found in the salt-surfactant mixtures that were heated for about twenty-four hours (Specimen III). FIG. 10A illustrates a sample that contains SDS and FIG. 10B illustrates a sample containing SBDS. The TEM images were obtained by placing the samples on TEM grids (supported by Silicon monoxide films). Additionally, the elemental composition of the nanoparticles was also analyzed by using EDS. EDS results confirmed that the nanoparticles observed in the TEM images were made of carbon. This establishes the formation of carbon nanoparticles in-situ during the thermocycling experiments for the eutectic salt samples mixed with surfactants.

Figure 11:
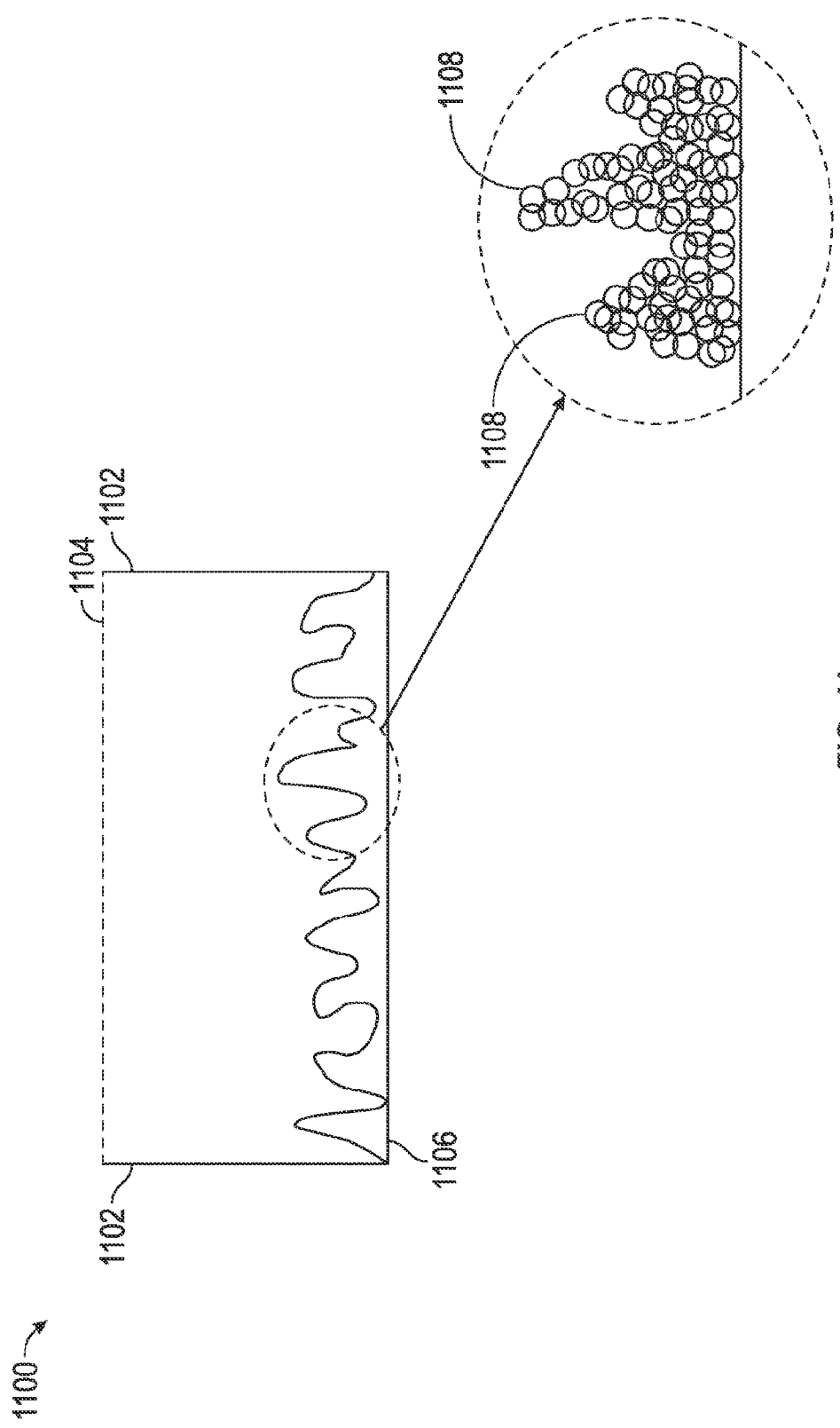
FIG. 11 is a schematic view of nanofins fabricated according to embodiments of disclosed herein and formed on an interior surface of a vessel.
Figure 12:
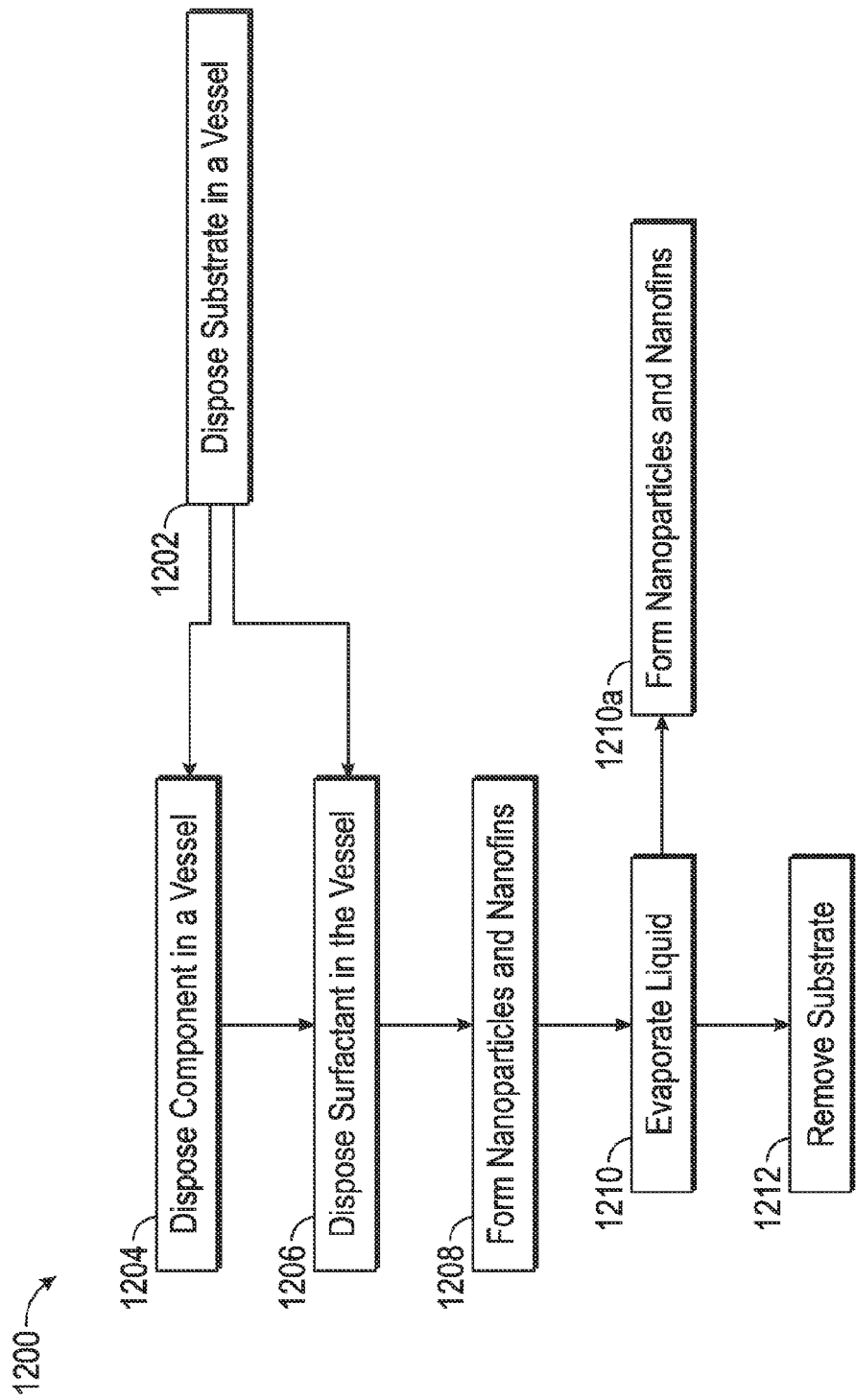
FIG. 12 is a flowchart of an embodiment of a method according to embodiments disclosed herein.

FIG. 11 is a schematic view of nanofins formed on an interior surface of a vessel. FIG. 12 is a flowchart of a method of forming nanofins in a vessel according to embodiments of the present disclosure. In some embodiments, for example at block 1202 of method 1200, a substrate may be disposed in a vessel 1100. As used herein, the term "vessel" may be used to describe a closed container, or a container with only one opening, or a container with more than one opening that may also be described as a conduit. The substrate may be disposed in any orientation that is suitable for the intended purpose, for example, flush with a side of the vessel such as the sidewalls 1102, the bottom 1106, or the top 1104. In some embodiments, the substrate may be place on its side, standing upright in the vessel 1100, if nanofin formation is desired on both sides of the substrate. Depending upon the embodiment, the top 1104 of the vessel 1100 may be an open top, a partially open top, or a closed top. In other embodiments, the top 1104 and the bottom 1106 of the vessel 1100 may be open, and this may be referred to as a conduit. In some embodiments, no substrate is disposed in the vessel 1100. In that embodiment, the precipitation discussed below may occur either on the interior surfaces of the vessel and/or in the liquid itself.

In an embodiment, at block 1204, a solvent is disposed in the vessel. The solvent can be a molten salt or other ionic liquids. The solvent can be water or other polar liquid. This molten salt may be a nitrate, chloride, carbonate, or fluoride, for example, when disposed in the vessel 1100. In some embodiments, block 1204 may be skipped and a surfactant such as sodium dodecyl sulfate (SDS) or sodium docedylbenzenesulfonate (SDBS) may be added at block 1206. It is appreciated that, in either embodiment whether or not molten salt or another type of solvent is used at block 1204, a substrate still may be disposed in the vessel 1100 at block 1202. The surfactant added at block 1206 may be an aqueous solution, comprising liquid, wherein the surfactant is, for example one of sodium dodecyl sulfate (SDS) and sodium docedylbenzenesulfonate (SDBS). At block 1208, a nanofluid is formed when nanoparticles are formed in-situ in the molten salt/surfactant mixture containing the surfactant. The nanoparticles referred to herein are formed in-situ, no nanoparticles are introduced to this solution in embodiments described herein, rather, the nanofluid is formed by the in-situ synthesis or precipitation of the nanoparticles which may each be less than or greater than 100 nm in size. In some embodiments, the nanofluid formed at block 1208 may not be further processed in the vessel 1100 and may instead be removed and used in a different vessel or application where nanofins and nanochannels may be formed.

In an embodiment, when the nanoparticles form at block 1208, the formation may be in response to an elevated temperature of the solution of surfactant or surfactant and molten salt. These nanoparticles may come together to form nanofins. A nanofin, as shown in FIG. 11, is a collection of nanoparticles that forms a nano-sized fin, and a plurality of nanofins may form grooves and/or channels in a vessel including a conduit. This formation of nanofins and channels may be used to better remove heat as fluids, gasses, and colloids are held in and/or pass through the vessel. Turning to FIG. 11, the bottom surface 1106 of the vessel 1100 has a plurality of precipitated nanoparticles 1108 that formed a plurality of nanofins 1106. The plurality of nanofins 1106 may be formed by the nanoparticles 1108 precipitating on each other, and/or the nanoparticles 1108 precipitation in solution and then attaching to other nanoparticles 1108. While the nanofins 1106 are only illustrated on the bottom surface 1106 and are shown in a two-dimensional view, it is understood that the nanoparticles may precipitate on any or all available surfaces including any substrates disposed in the vessel at block 1202. The expanded view in FIG. 11 shows the plurality of nanoparticles 1108 that have come together to form nanofins 1106. In an embodiment, the plurality of nanofins 1106 form in a manner such as to create channels or grooves along each surface 1106, 1102, 1104 and the substrate (if present). These channels or grooves may be used as discussed above with respect to controlling heat along a surface or in a particular device. Turning back to FIG. 12, at block 1210 the liquid from the nano-fluid is evaporated or otherwise removed, for example, using a hot plate, oven, vacuum pump, evacuated chamber, or other method. In some embodiments, all of the liquid may be removed at block 1210, and in alternate embodiments only a portion of liquid may be removed. In other embodiments, block 1210 may comprise more than one step wherein the liquid is removed in stages and/or at predetermined intervals. In an embodiment, the precipitation of nanoparticles may occur at block 1210a subsequent to the evaporation of at least some of the liquid at block 1210. This precipitation at block 1210a may occur instead of, or in addition to, the formation of nanoparticles at block 1208. The precipitation may occur on the substrate and/or the inside surface(s) of the vessel, and/or in the liquid itself.

The nanoparticles that form nanofins when precipitated at block 1208 and/or 1210 may be from 1 nm in width and/or length to 100,000 nm in width and/or length. It is understood that nanofins are agglomerations of nanoparticles, so a nanofin may comprise any combination of dimensions as appropriate based upon the dimensions of the nanoparticles in the solution. At block 1212, if a substrate was disposed in the vessel at block 1202, the substrate may be removed. The substrate removed at block 1212 may be a test sample, or may be a wafer or other component or subassembly that may be used as-is or that may be further processed.

In an embodiment, the in-situ formation of nanoparticles in the solution results in different material properties, that is, the nanoparticles formed in-situ change and in some cases improve the properties of the solution. Properties such as energy storage capacity, specific heat capacity, thermal conductivity, density, viscosity, electrical conductivity, ionic conductivity, catalytic properties, chemical reactivity, optical transmissivity, optical reflectivity, optical absorptivity, and radiation cross-section (absorptivity and transmissivity of nuclear materials in nuclear reactions), may be improved by in-situ synthesis of the nanoparticles. In addition, properties including transmissivisity, polarizability, reflectivity and absorptivity of electromagnetic radiation waves and particles may also be positively impacted. Also in an embodiment, the formation of nanofins at the interface between different phases—such as solid and liquid may result in different material properties. This may be an improvement in properties such as energy storage capacity, specific heat capacity, thermal conductivity, density, viscosity, electrical conductivity, as well as transmissivisity, polarizability, reflectivity and absorptivity of electromagnetic radiation waves and particles.

Bare silicon wafers on which pure water and nanofluids are tested have inherently atomic scale roughness; so, there is no surface roughness effect when performing experiments on pure water since there is nothing to precipitate on the heat exchanging surface. However, nanoparticles may precipitate on heat exchanging surfaces forming nano-scale protrusions. These nano-scale protrusions enhance the effective surface area for the heat exchanging surfaces, and thus behave like nanofins. However, prior studies in the published literature used nanofluids that had nanoparticles introduced into the fluid, and did not use in-situ fabrication of nanoparticles as discussed herein. A liquid or gas may flow through the conduits formed by the nanofins created by the precipitation of the nanoparticles that can enhance the transport of mass, energy and chemical species (diffusion). In some embodiments, excessive precipitation of nanoparticles can lead to opposite behavior—that can degrade the transport of mass, energy and chemical species (diffusion) as well as catalytic, properties. Hence, the nanoparticles formed in-situ can be used to achieve tunable properties for the flow in the conduits formed by the precipitation of the nanoparticles. A liquid or gas may flow through the conduits formed by the nanofins created by the precipitation of the nanoparticles that can enhance the transport of mass, energy, and chemical species (diffusion) as well as catalytic properties. The methods discussed herein may enable surfaces to be more readily prepared and changed over, for example, if a particular vessel is used with a first fluid and then with a second fluid or gas, the property differences between the two may make it desirable to remove the nanofins from the vessel and re-form the nanofins. In other embodiments, the methods discussed herein create robust structures that may be used for an extended length of time without maintenance or with reduced maintenance, thereby creating more up-time for the process in which the vessel is utilized.

Figure 13A:
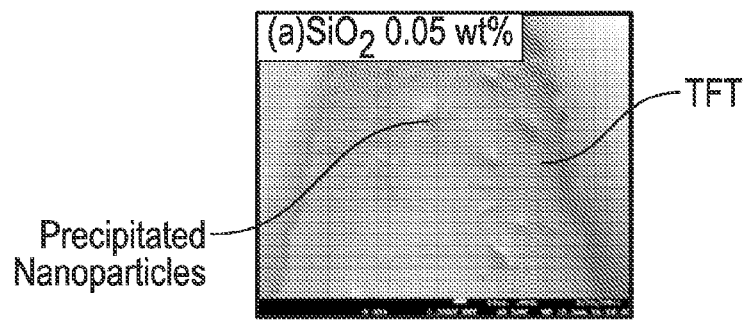
FIGS. 13A-13F are SEM images of nanoparticles precipitated in-situ according to embodiments disclosed herein.
Figure 13B:
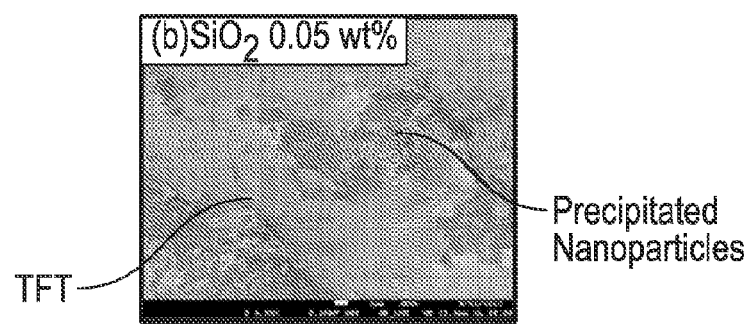
Figure 13C:
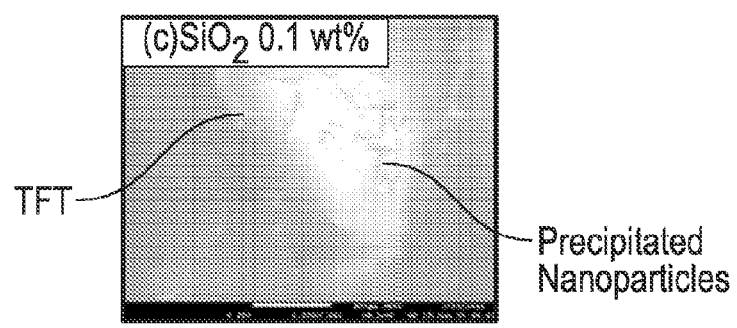
Figure 13D:
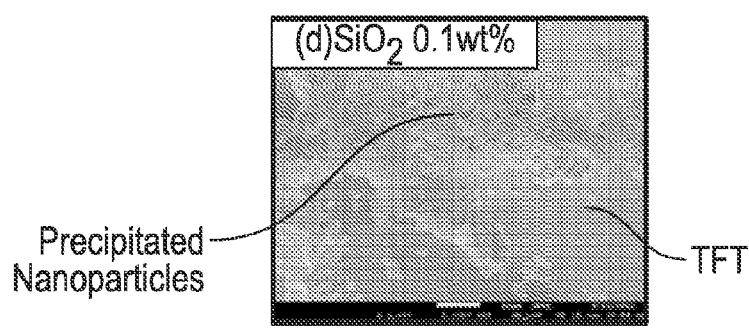
Figure 13E:
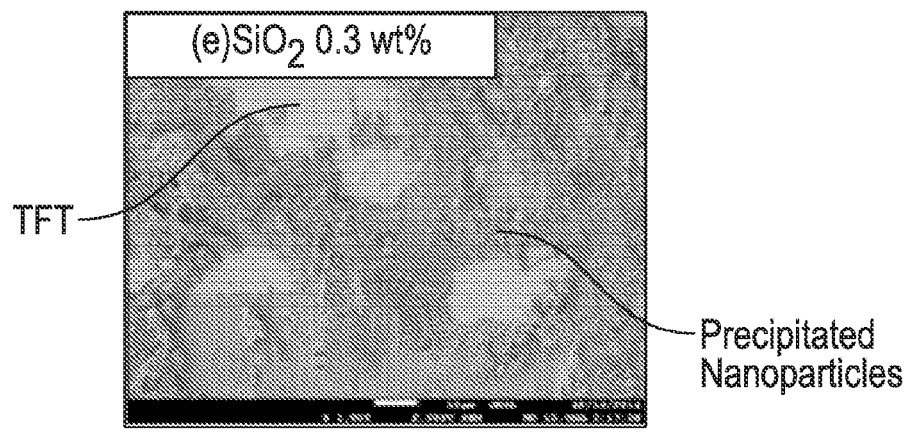
Figure 13F:
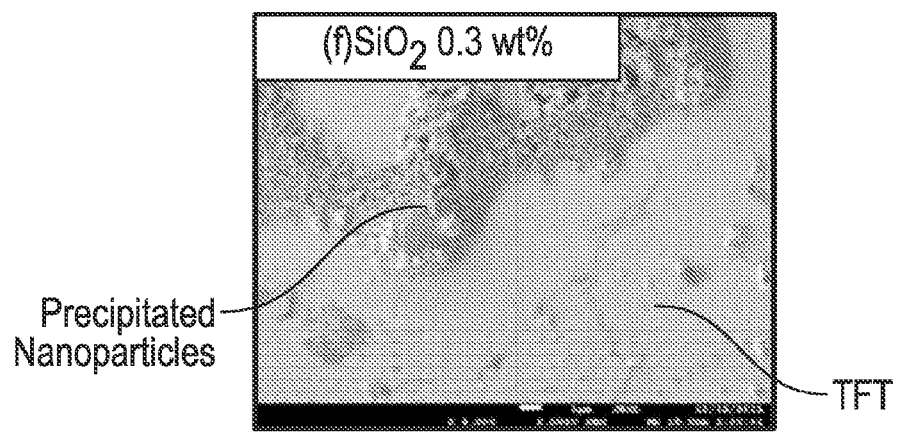

FIGS. 13A-13F are SEM images of nanoparticles precipitated in-situ according to embodiments of the present disclosure. In an embodiment, nanoparticles may be precipitated in-situ according to, for example, the method in FIG. 12. In one example, nanoparticles were precipitated in-situ near a thin film transistor (TFT) array. During a series of forced convective heat transfer using $SiO_2$ nanofluids where the nanofluids were formed when the nanoparticles precipitated in-situ, nanoparticles and nanofins precipitated both near the TFT array and away from the TFT array. FIGS. 13A-13F are SEM images that show precipitation of nanoparticles on the bottom surface of the microchannel at the locations near the TFT array after performing forced conductive heat transfer experiments using $SiO_2$ nanofluids. FIGS. 13A and 13B illustrate nanoparticles precipitated on the bottom surface of the microchannel and those that may adhere to the bottom surface of the microchannel as they precipitate in-situ, these images are from a nanofluid containing $SiO_2$ nanoparticles at a mass concentration of 0.05%. FIG. 13B is 10× the magnification of FIG. 13A. FIGS. 13C and 13D illustrate nanoparticles precipitated on the bottom surface of the microchannel and those that may adhere to the bottom surface of the microchannel as they precipitate in-situ, these images are from a nanofluid containing $SiO_2$ nanoparticles at a mass concentration of 0.1%. FIG. 13D is 10× the magnification of FIG. 13 C. FIGS. 13E and 13F illustrate nanoparticles precipitated on the bottom surface of the microchannel and those that may adhere to the bottom surface of the microchannel as they precipitate in-situ, these images are from a nanofluid containing $SiO_2$ nanoparticles at a mass concentration of 0.3%. FIG. 13F is 10× the magnification of FIG. 13E. FIGS. 13A-13F are illustrative, similar experiments were performed using varying concentrations of $TiO_2$ and similar in-situ precipitation and flow behavior was observed. It is noted that the in-situ precipitation of nanoparticles may occur on interior surfaces, transitional surfaces which the nanofluid may be in contact with, and/or within the nanofluid itself. As seen in FIGS. 13A-13F, even if nanoparticles precipitate within the nanofluid and not on a surface, these nanoparticles may still form nanofins and contribute to enhancement or degradation of transport of mass, energy and chemical species (diffusion) as discussed above. These nanoparticles may be initially used for heat transfer initially and then subsequently or simultaneously for insulation when the heat transfer properties degrade, thereby increasing the life of the coating.

The cooling efficiency of thermal management platforms in single phase flows have focused on enhancing the thermal properties of the heat transfer media (i.e. the coolant or other aqueous solution) or by increasing the effective surface area available for transferring thermal energy. Using the methods and systems discussed above, this may be accomplished by the formation of nanofins from nanoparticles. Such nanofins may form the nanogrooves and nanochannels discussed above that increase the surface area of the surface(s) they form on. This increased surface area may increase the cooling efficiency of various thermal management platforms discussed above.

Exemplary embodiments are disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). The term "about" as used herein to discuss properties and characteristics of materials and machine settings may comprise the value or range of values stated +/−10%, where the value as well as each of the high and the low end of the range may vary by +/−10%, in some cases to account for processing conditions or equipment configurations. For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of broader terms such as "comprises," "includes," and "having" should be understood to provide support for narrower terms such as "consisting of," "consisting essentially of," and "comprised substantially of." Accordingly, the scope of protection is not limited by the description set out above but is defined by the claims that follow, that scope including all equivalents of the subject matter of the claims. Each and every claim is incorporated into the specification as further disclosure, and the claims are exemplary embodiment(s) of the present invention.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the embodiments described herein. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A method for fabricating nanostructures comprising:
   (a) forming a homogeneous solution in a vessel, wherein the homogenous solution comprises a first component, or a first component and a second component, wherein the first component and the second component do not comprise nanoparticles, wherein the first component comprises a surfactant, and wherein the second component comprises a salt;
   (b) evaporating at least some of a liquid in the homogenous solution after (a);
   (c) precipitating a first plurality of nanoparticles from the homogeneous solution in response to (a) or (b), wherein the first plurality of nanoparticles is formed via chemical degradation of the surfactant, and wherein the first plurality of nanoparticles is formed on an interior surface of the vessel or in the homogeneous solution spaced apart from the interior surface of the vessel; and
   (d) forming a first plurality of nanofins on the interior surface of the vessel with the first plurality of nanoparticles after (c).

2. The method of claim 1, wherein each precipitated nanoparticle of the first plurality of nanoparticles is a carbon nanoparticle having a size less than about 100 nm.

3. The method of claim 1, wherein the second component is a molten salt selected from alkali-nitrate salts, alkali-carbonate salts, alkali-chloride salts halo en derivatives thereof or eutectic mixtures thereof.

4. The method of claim 1, wherein the salt is a nitrate, a chloride, a carbonate, or a fluoride.

5. The method of claim 1, comprising both the first component the second component.

6. The method of claim 5, wherein the surfactant comprises sodium dodecyl sulfate (SDS) or sodium docedylbenzenesulfonate (SDBS).

7. The method of claim 1, further comprising:
   (e) disposing a substrate in the vessel before disposing the first component or the second component in the vessel;
   (f) precipitating a second plurality of nanoparticles from the homogeneous solution onto the substrate in response to (a) or (b);
   (g) forming a second plurality of nanofins on the substrate with the second plurality of nanoparticles; and
   (h) removing the substrate from the vessel after (g).

8. The method of claim 1, wherein (b) comprises heating the homogenous solution to a temperature between about 25° C. and about 600° C.

9. The method of claim 8, wherein (b) comprises maintaining the homogenous solution at a temperature between about 25° C. and about 600° C. for about four hours to about twenty-four hours.

10. The method of claim 8, wherein (b) comprises maintaining the homogenous solution at a pressure lower than the atmospheric pressure for rapid evaporation of the liquid while maintaining the homogenous solution at the temperature between about 25° C. and about 600° C. for about four hours to about twenty-four hours.

11. The method of claim 1, further comprising:
   mixing the first plurality of nanoparticles precipitated from the homogenous solution with a plurality of particles having a size greater than about 100 nm.

12. A method for fabricating nanostructures in-situ, the method comprising:
   (a) forming a solution in a vessel, wherein the solution comprises a surfactant;

(b) after (a), precipitating a first plurality of nanoparticles from the solution onto an inner surface of the vessel within the solution, or both;

(c) evaporating at least some of a liquid in the solution after (b);

(d) forming, in response to (b) or (c), a plurality of nanofins on a portion of the inner surface of the vessel with the first plurality of nanoparticles precipitated from the solution, wherein the first plurality of nanoparticles is formed via chemical degradation of the surfactant; and (e) forming a first plurality of channels on the portion of the inner surface of the vessel, wherein each channel of the first plurality of channels comprises at least some nanofins of the plurality of nanofins.

13. The method of claim 12, wherein the surfactant s comprises sodium dodecyl sulfate (SDS) or sodium docedyl-benzenesulfonate (SDBS).

14. The method of claim 12, wherein (c) comprises heating the solution to a temperature between about 10° C. to about 600° C.

15. The method of claim 14, wherein (c) further comprises maintaining the solution at a temperature between about 10° C. to about 600° C. for about four hours to about twenty-four hours.

16. The method of claim 12, further comprising:
(e) prior to forming the solution in the vessel in (a), disposing a substrate in the vessel;
(f) precipitating a second plurality of nanoparticles from the solution in response to (a) or (b); and
(g) forming a second plurality of nanofins on the substrate with the second plurality of nanoparticles precipitated from the solution.

17. A method for fabricating nanostructures comprising:
(a) disposing a substrate in a vessel and contacting an inner surface of the vessel with the substrate;
(b) disposing a first component or both a first component and a second component in the vessel to form a homogeneous solution in the vessel, wherein the first component and the second component do not comprise nanoparticles, wherein the first component comprises a surfactant, and wherein the first component or the second component is a solution;
(c) removing at least some of a liquid from the homogenous solution after (b);
(d) precipitating a plurality of nanoparticles from the homogenous solution onto the inner surface of the vessel and the substrate in response to (b) or (c), wherein the plurality of nanoparticles is formed via chemical degradation of the surfactant; and
(e) forming a plurality of nanofins on the inner surface of the vessel and on the substrate with the plurality of nanoparticles precipitated from the solution in (d).

18. The method of claim 17, wherein each nanoparticle has a size less than about 100 nm.

19. The method of claim 17, wherein the first second component comprises a salt.

20. The method of claim 19, wherein the salt is a nitrate, a chloride, a carbonate, or a fluoride.

21. The method of claim 17, wherein the homogeneous solution comprises both the first component and the second component.

22. The method of claim 17, wherein the surfactant comprises sodium dodecyl sulfate (SDS) or sodium docedyl-benzenesulfonate (SDBS).

23. A method for fabricating nanofins from nanoparticles formed in-situ comprising:
(a) forming a homogeneous solution comprising a first component and a second component in a vessel, wherein the first component comprises a plurality of nanoparticles formed in-situ in the homogeneous solution via chemical degradation of a surfactant;
(b) precipitating a first plurality of nanoparticles from the homogeneous solution onto an inner surface of the vessel or in the homogeneous solution;
(c) forming a first plurality of nanofins on an inner surface of the vessel with the first plurality of nanoparticles.

24. A method for fabricating nanostructures, comprising:
(a) forming a homogeneous solution in a vessel, wherein the homogenous solution comprises a first component comprising a surfactant, a second component comprising a molten salt, and a third component comprising a catalyst, wherein the first component and the second component do not comprise nanoparticles;
(b) evaporating at least some of a liquid in the homogenous solution after (a);
(c) precipitating a first plurality of nanoparticles from the homogeneous solution in response to (a) or (b), wherein the first plurality of nanoparticles is formed via formed on an inner surface of the vessel or in the homogeneous solution;
(d) forming a first plurality of nanofins with the first plurality of nanoparticles, wherein the first plurality of nanofins is formed on the inner surface of the vessel with the first plurality of nanoparticles.

* * * * *